US010865278B2

(12) United States Patent
Grzelakowski et al.

(10) Patent No.: US 10,865,278 B2
(45) Date of Patent: Dec. 15, 2020

(54) VESICLES FORMED FROM BLOCK COPOLYMERS, AND NOVEL BLOCK COPOLYMERS

(71) Applicants: APPLIED BIOMIMETIC A/S, Nordborg (DK); THE PENN STATE RESEARCH FOUNDATION, University Park, PA (US)

(72) Inventors: Mariusz Piotr Grzelakowski, Gaithersburg, MD (US); Manish Kumar, State College, PA (US); Ian T. Sines, East Bridgewater, MA (US)

(73) Assignees: APPLIED BIOMIMETIC A/S, Nordborg (DK); THE PENN STATE RESEARCH FOUNDATION, University Park, PA (US)

( * ) Notice: Subject to any disclaimer, the term of this patent is extended or adjusted under 35 U.S.C. 154(b) by 0 days.

(21) Appl. No.: 15/560,961

(22) PCT Filed: Mar. 24, 2016

(86) PCT No.: PCT/EP2016/056504
§ 371 (c)(1),
(2) Date: Sep. 22, 2017

(87) PCT Pub. No.: WO2016/151073
PCT Pub. Date: Sep. 29, 2016

(65) Prior Publication Data
US 2018/0079869 A1    Mar. 22, 2018

Related U.S. Application Data

(60) Provisional application No. 62/137,320, filed on Mar. 24, 2015.

(51) Int. Cl.
C08G 81/02    (2006.01)
C08G 73/02    (2006.01)
(Continued)

(52) U.S. Cl.
CPC .............. *C08G 81/024* (2013.01); *A61K 8/14* (2013.01); *A61K 8/64* (2013.01); *A61K 8/90* (2013.01);
(Continued)

(58) Field of Classification Search
None
See application file for complete search history.

(56) References Cited

U.S. PATENT DOCUMENTS 5,807,944 A    9/1998    Hirt et al.
6,723,814 B2   4/2004    Meier et al.
(Continued)

FOREIGN PATENT DOCUMENTS

WO    WO 00/37541 A1    6/2000
WO    WO 2008/153966 A1    12/2008
WO    WO 2015/166038 A1    11/2015

OTHER PUBLICATIONS

Dissertation of Zofia Hordyjewicz-Baran, "Synthesis and Study of the Aggregation Behavior of Hyrophilically Modified Polybutadienes," *Universitat Potsdam*, 105 pgs. (May 2008).
(Continued)

*Primary Examiner* — Krishnan S Menon
(74) *Attorney, Agent, or Firm* — Christensen, Fonder, Dardi & Herbert PLLC

(57) ABSTRACT

Vesicles formed from a block copolymer comprising at least one (poly)2-$C_{1-3}$alkyl-2-oxazoline block and at least one polybutadiene block; and membranes comprising such vesicles. Block copolymers comprising at least one (poly) 2-$C_{1-3}$alkyl-2-oxazoline block and at least one polybutadiene block, provided that the copolymer is not the diblock copolymer consisting of 40 butadiene units and 190 2-methyl-2-oxazoline units terminated by a hydroxy group, are novel, and also form part of the invention.

18 Claims, 5 Drawing Sheets

(51) Int. Cl.
| | |
|---|---|
| A61K 8/14 | (2006.01) |
| A61K 8/64 | (2006.01) |
| A61K 8/90 | (2006.01) |
| A61K 9/127 | (2006.01) |
| A61K 47/34 | (2017.01) |
| A61K 47/42 | (2017.01) |
| B01D 69/12 | (2006.01) |
| B01D 71/24 | (2006.01) |
| B01D 71/56 | (2006.01) |
| B01D 71/80 | (2006.01) |
| B01D 71/82 | (2006.01) |
| C02F 1/44 | (2006.01) |
| C08L 87/00 | (2006.01) |

(52) U.S. Cl.
CPC .......... *A61K 9/1271* (2013.01); *A61K 9/1277* (2013.01); *A61K 47/34* (2013.01); *A61K 47/42* (2013.01); *B01D 69/125* (2013.01); *B01D 71/24* (2013.01); *B01D 71/56* (2013.01); *B01D 71/80* (2013.01); *B01D 71/82* (2013.01); *C02F 1/44* (2013.01); *C08G 73/0233* (2013.01); *C08L 87/005* (2013.01)

(56) References Cited

U.S. PATENT DOCUMENTS

| | | |
|---|---|---|
| 6,916,488 B1 | 7/2005 | Meier et al. |
| 2008/0305149 A1 | 12/2008 | Hirt et al. |
| 2011/0046074 A1 | 2/2011 | Kumar et al. |
| 2012/0129270 A1 | 5/2012 | Nallani et al. |
| 2017/0113193 A1 | 4/2017 | Grzelakowski |
| 2017/0166704 A1 | 6/2017 | Grzelakowski |

OTHER PUBLICATIONS

Xu, Shengqing, et al., "Synthesis and characterization of diblock copolymer of butadiene and 2-ethyl-2-oxazoline," *Science in China (Series B)*, vol. 41, No. 2, pp. 194-201 (Apr. 1998).

Wang, Hong Lei, et al., "Mechanically robust and highly permeable AquaporinZ biomimetic membranes," *Journal of Membrane Science*, vol. 434, pp. 130-136 (2013).

VESICLES FORMED FROM BLOCK COPOLYMERS, AND NOVEL BLOCK COPOLYMERS

PRIORITY CLAIM

The present application is a National Phase entry of PCT Application No. PCT/EP2016/056504, filed Mar. 24, 2016, which claims priority from U.S. Provisional Patent Application No. 62/137,320, filed Mar. 24, 2015, the disclosures of which are hereby incorporated by reference herein in their entirety.

FIELD OF THE INVENTION

This invention relates to vesicles formed from block copolymers, specifically, from block copolymers of butadiene and 2-$C_{1-3}$alkyl-2-oxazoline. The invention also relates to membranes formed from such vesicles. Most polybutadiene/(poly)2-$C_{1-3}$alkyl-2-oxazoline block copolymers are novel, and these novel block copolymers also form part of the invention.

BACKGROUND OF THE INVENTION

Vesicles and cells in nature are nano-containers built by amphiphilic lipids and supported by cholesterol. Amphiphilic block copolymers have been studied as a synthetic alternative for use in the production of artificial vesicles, but the number of block copolymers studied has been very small, focussed mainly on copolymers of (poly)2-methyl-2-oxazoline (PMOXA)/poly(dimethylsiloxane) (PDMS); poly (ethylene glycol) (PEG)/PMOXA; and PEG/polybutadiene (PB). WO 00/37541 relates to novel amphiphilic block copolymers comprising a hydrophilic segment and a hydrophobic segment, while U.S. Pat. No. 6,916,488 discloses vesicles made from amphiphilic copolymers. The vesicles of U.S. Pat. No. 6,916,488 may be used for drug delivery or as nanoreactors, and may have membrane proteins incorporated into their walls; the copolymers can be AB or ABA block copolymers where one of A and B is hydrophilic and the other is hydrophobic. The authors of U.S. Pat. No. 6,916,488 mention a wide range of possible candidates for A and B, but the only polymer exemplified is poly(2-methyloxazoline)-poly(dimethylsiloxane)-poly(2-methyl-oxazoline) (PMOXA-PDMS-PMOXA). U.S. Pat. No. 6,723,814 relates to planar membranes formed from amphiphilic copolymers. US 2008/0305149 discloses the use of block copolymer vesicles having mucoadhesive groups, for mucosal delivery of drugs.

WO 2004/011600 discloses that aquaporins may be incorporated into tri-block copolymers to form a membrane which will only pass water, excluding all contaminants. Since this disclosure, much work has been carried out to develop membranes incorporating transmembrane proteins, and some of these have attempted to use block copolymer vesicles. For example, WO 2013/043118 discloses the use of vesicles, either containing or not containing aquaporins, embedded in a polyamide layer on a support membrane. The copolymer may be PMOXA-PDMS-PMOXA or a number of other copolymers, i.e. EO-PO, EO-Bd, EO-PDMS and EO-BO, where EO is ethylene oxide, PO is propylene oxide, Bd is butadiene, and BO is butylene oxide.

Amphiphilic copolymers of polyethylene glycol and butadiene are well known, see for example M. A. Hillmyer and F. S. Bates, "Synthesis and Characterization of Model Poly-alkane-Poly(ethyleneoxide) Block Copolymers", Macromolecules, 29, 6994 (1996)]. However, they have a number of disadvantages. For example, ethylene oxide is gaseous which makes it difficult to handle, especially when using larger quantities, as it is a flammable, highly toxic and highly regulated compound. Further, it is not easy to functionalise or to cross-link ethylene oxide.

A dissertation by Zofia Hordyjewicz-Baran of the University of Potsdam, entitled "Synthesis and Study of the Aggregation Behavior of Hydrophilically Modified Polybutadienes", available from the Max Plank Institute for Colloid and Interface Research and at http://www.mpikg.mpg.de/48071/HORDYJEWICZ-BARAN_Dissertation.pdf, describes hydrophilically modified butadiene homopolymers and block copolymers. Hydroxy-terminated $PB_{40}$-b-$PMOXA_{190}$ copolymer is amongst the copolymers made, and this copolymer is reacted with 2-mercaptoethylamine hydrochloride, which reacts with the double bonds present in the polybutadiene block. There is no suggestion that vesicles could or should be made from this copolymer, neither is there any suggestion that the end group of this copolymer should be modified in any way.

We have now found that block copolymers comprising at least one (poly)2-$C_{1-3}$alkyl-2-oxazoline block and at least one polybutadiene block, and particularly such copolymers having specific end groups, have major advantages when used for vesicle formation and in membranes. Specifically, the block copolymers form vesicles very readily; it is easy to tailor the size of the vesicles; it is easy to stabilise the vesicles; and the polymers can be readily functionalised to perform a range of reactions. Further, the permeability of the block copolymers is inherently low, and can be adjusted to be very low, which makes the polymers valuable for a number of applications, including use in vesicles for delivery of substances including for example drugs and cosmetics, and for use in membranes.

SUMMARY OF THE INVENTION

The invention provides vesicles formed from a block copolymer comprising at least one (poly)2-$C_{1-3}$alkyl-2-oxazoline block and at least one polybutadiene block. Also provided are vesicles having transmembrane proteins incorporated therein, and filtration membranes comprising such protein-containing vesicles. Most block copolymers comprising at least one (poly)2-$C_{1-3}$alkyl-2-oxazoline block and at least one polybutadiene block are novel, and the invention further provides these novel polymers per se. Specifically, the present invention provides a block copolymer comprising at least one (poly)2-$C_{1-3}$alkyl-2-oxazoline block and at least one polybutadiene block, provided that the copolymer is not the diblock copolymer consisting of 40 butadiene units and 190 2-methyl-2-oxazoline units terminated by a hydroxy group, i.e. is not diblock hydroxy-terminated $PB_{40}$-b-$PMOXA_{190}$.

DETAILED DESCRIPTION OF THE INVENTION

Block Copolymers

The block copolymer used in the present invention comprises at least one (poly)2-$C_{1-3}$alkyl-2-oxazoline (PAOXA) block and at least one polybutadiene (PB) block. The polymer is suitably a diblock copolymer AB or especially BA, or a triblock copolymer ABA, in which PAOXA forms the A block(s) and PB forms the B block.

Block copolymers which comprise at least one (poly)2-$C_{1-3}$alkyl-2-oxazoline (PAOXA) block and at least one polybutadiene (PB) block have a number of properties which make them particularly suitable for use in the formation of vesicles.

All such copolymers save hydroxy-terminated $PB_{40}$-b-$PMOXA_{190}$ are novel and form part of the present invention. Suitably copolymers according to the invention contain less than 190 2-alkyl-2-oxazoline units in the PAOXA block. The specific hydroxy-terminated $PB_{40}$-b-$PMOXA_{190}$ polymer disclosed in the dissertation by Hordyjewicz-Baran referred to above is highly hydrophilic, containing a large preponderance of hydrophilic MOXA units compared with hydrophobic butadiene units. Particularly valuable for use in the present invention are copolymers containing a greater proportion of hydrophobic butadiene units, for example copolymers in which the number of butadiene units in the PB block is at least half the number of 2-alkyl-2-oxazoline units in the PAOXA block, for example copolymers in which the number of butadiene units in the PB block is at least equal to the number of 2-alkyl-2-oxazoline units in the PAOXA block, especially copolymers in which the number of butadiene units in the PB block is greater than twice the number of 2-$C_{1-3}$alkyl-2-oxazoline units in the PAOXA block. For example the ratio of the number of butadiene units in the PB block to the number of 2-$C_{1-3}$alkyl-2-oxazoline units in the PAOXA block may be greater than 1:1.75, which is equivalent to a hydrophilic to lipophilic ratio of 17.64.

In absolute terms, the copolymer of the invention preferably contains at least 5, for example 5, 6, 7, 8, 9, 10, 11, 12, 13, 14 or 15 butadiene units, for example up to 200, especially up to 160, and most especially up to 120, butadiene units; and at least 5, for example 5, 6, 7, 8, 9, 10, 11, 12, 13, 14 or 15 2-$C_{1-3}$alkyl-2-oxazoline units, for example up to 189, especially up to 180, for example up to 160, and most especially up to 120, 2-$C_{1-3}$alkyl-2-oxazoline units.

Separately from or in addition to any one or more of the features above, in specific embodiments, the invention provides a copolymer which comprises at least one PAOXA block and at least one PB block, provided that the polymer has end groups which are other than —OH, particularly, provided that the polymer has at least one end group at the end of a (poly)2-$C_{1-3}$alkyl-2-oxazoline block which is other than —OH; and/or in which the copolymer is a triblock copolymer, and/or in which the PAOXA block is less than 190; and/or in which the ratio of the number of butadiene units to the number of 2-$C_{1-3}$alkyl-2-oxazoline units is greater than 4:19; and/or the $C_{1-3}$alkyl group in the PAOXA block is $C_{2-3}$alkyl.

The $C_{1-3}$alkyl group in the (poly)2-$C_{1-3}$alkyl-2-oxazoline block may be methyl, ethyl or propyl or a mixture thereof. Preferably the or each (poly)2-$C_{1-3}$alkyl-2-oxazoline block is a (poly)2-methyl-2-oxazoline block. Throughout this specification, unless the context requires otherwise, any mention of $C_{1-3}$alkyl should be understood to include a specific mention of methyl.

The Dissertation by Hordyjewicz-Baran referred to above discloses one specific method of preparing block copolymers. Synthesis of block copolymers by polymerisation is well known, and the length of the one or more segments which are to be copolymerized on the starting segment can be easily controlled by controlling the amount of monomer which is added for the copolymerization, and/or by the addition of suitable chain-terminating capping agents. In this way the size of the segments and their ratio can easily be controlled.

It is known in the art that the absolute and relative lengths of the blocks are important in determining the suitability of copolymers for forming vesicles (so called polymer hydrophobic ratio). Further, as one of the intended uses of the vesicles according to the invention is in the formation of membranes from vesicles having transmembrane proteins incorporated therein as discussed below, the length of the blocks in polymers intended for this application is preferably such that the thickness of the vesicle wall is broadly comparable with the length of the transmembrane protein so that the protein can be readily incorporated into the vesicle walls without the channel becoming blocked. For example the thickness of the vesicle wall may be in the range of from 1 nm to 50 nm. The length of the hydrophobic polybutadiene block is particularly important, and this should preferably be no greater than 200 repeat units.

The two end groups on a polymer chain may be the same as each other, or different. If the B block of a BA diblock copolymer is polybutadiene, the end group of that block will generally, following synthesis, contain a group which depends on the initiator used for the PB polymerisation. For example, if an alkyl lithium initiator R—Li is used, it will contain an alkyl group R. The initiator may for example be sec-butyl lithium, in which case the end group will be a sec-butyl group. Each repeating unit of the PB block will of course contain a C═C double bond. The end group of the A (PAOXA) group will depend on the means used to terminate the growing polymer chain. In an ABA tri-block copolymer, both end groups will be at PAOXA groups, while the middle B block will, in the absence of cross-linking, contain C═C double bonds.

In a preferred embodiment of the invention, the PAOXA block of the block copolymer contains end groups which are other than an —OH group. Choice of suitable end-groups may promote vesicle formation, or may provide functionality for onward reaction of the polymer. Specifically, preferred end groups include carboxyl groups and activated carboxyl groups; amine groups; methacrylate groups; thiol groups; azide groups; and alkyne groups. In one preferred embodiment, the block copolymer contains at least one carboxyl end group at the end of the PAOXA block. In another preferred embodiment, the block copolymer contains an end group at the end of the PAOXA group which includes an —$NH_2$ group. Especially preferred are end groups which contain both an —$NH_2$ and an —NH— group, i.e. the end group includes both a primary and a secondary amine group.

Required end groups may be present following initial synthesis of the copolymer, or may be introduced following the copolymer synthesis. If not present following initial synthesis, it is possible to introduce an appropriate end group by suitable reactions at the end of the relevant block. For this purpose, the polymerization of the growing segment may be terminated after a suitable chain length is reached and the initiator group present at the chain end capped. For example, capping using water will result in an —OH end group, while capping with an appropriate amine will lead to an amine end group. Alternatively, capping may be carried out using any other desired terminator, and the required end group may be introduced using known chemistry. For example, termination may be carried out using KOH/MeOH or unsaturated groups at the end of the growing segment. The end group(s)s may then be reacted using conventional chemistry to introduce the required groups.

In a particularly preferred embodiment of the invention, the block copolymer is terminated by at least one end group X having the formula —NHR in which R represents an alkyl group which may be straight-chain or branched having from 1 to 6 carbon atoms substituted by at least one, for example 1, 2 or 3, —$NH_2$ groups. Preferably such an end group X has the formula —NH—CH—$(NH_2)_2$ or, preferably, —NH—$(CH_2)_n$—$NH_2$, in which n is an integer from 2 to 6, preferably 2 to 4, especially 2. Such end groups may be introduced by reacting a polymer having —OH end groups with a suitable reactive amine $NH_2R$, for example a diamine, for example $H_2N$—$(CH_2)_n$—$NH_2$, especially $H_2N$—$(CH_2)_2$—$NH_2$, or triamine, for example $N.([CH_2]_nNH_2)_3$ or $CH.([CH_2]_nNH_2)_3$, for example $CH(NH_2)_3$ or tris(3-aminopropyl)amine. Branched oligomeric imines may also be used. Alternatively, as mentioned above, the growing polymer chain can be capped using an appropriate amine.

More information on end groups is given in the "Membranes" section below.

Vesicles

Block copolymers comprising at least one (poly)2-$C_{1-3}$alkyl-2-oxazoline block and at least one polybutadiene block have been found to be particularly suitable for the formation of vesicles, and the present invention provides vesicles formed from such copolymers.

The vesicles of the invention may be prepared from the block copolymers by methods well known in the art. Generally, these methods involve either solvent displacement or solvent-free rehydration. In solvent displacement methods, the block copolymer is dissolved in an organic solvent before mixing with water. After mixing, and optionally removing the organic solvent, spontaneous self-assembly of vesicles results. In solvent-free rehydration, dry block copolymer is brought into contact with an aqueous medium whereupon hydration results in the spontaneous self-assembly of vesicles. In a special case of solvent-free rehydration, the thin-film rehydration process, block copolymer is dissolved in an organic solvent which is then removed under conditions such that a thin film is formed. This film is then hydrated by contacting with water, and vesicles are formed by self-assembly. An alternative known method of vesicle preparation involves the use of sonication, the degree of sonication determining the initial size of the vesicles formed.

The block copolymers of the present invention often tend initially to form relative large vesicles (which may be described as "Giant Unilamellar Vesiclses", GUVs). GUV's generally have diameters of from about 1 to 20 microns. Vesicles having a desired size and low polydispersity can be obtained from the initially formed population of vesicles by known methods, for example by extrusion of large uni- and multi-lamellar polydisperse vesicles through one or more membranes of known pore size. Track etched polycarbonate membranes, for example Isopore (Trade Mark) membranes available from Millipore, are suitable for this purpose. It has been found that it is easier to tailor the size of vesicles made from the copolymers of the present invention than it is when making vesicles from known copolymers. Specifically, it is easier to make GUVs using the copolymers of the present invention than when using known copolymers. The optimal size of the vesicles prepared and used in the present invention will depend on their intended application. For example, the vesicles may have an average diameter in the range of from 30 to 10,000, preferably 50 to 1000, more preferably 100 to 400, especially from 150 to 250, nm.

The propensity of block copolymers to form vesicles, rather than other self-assembly structures such as micelles, depends on the absolute and relative sizes of the blocks; this is known in the art. It also depends on the nature of the polymer end-groups, and this is not known in the art. For example, when the polymer is terminated with —OH groups, and when the blocks are relatively high molecular weight, micelles tend to be formed, which means that lower molecular weight polymers are preferred if vesicles are required. Surprisingly, the presence of an end group which is a carboxyl or an amine group, particularly an amine group including both an —$NH_2$ and an —NH— group, facilitates the formation of vesicles.

If required, vesicles according to the invention may be internally cross-linked via the double bonds in the PB block. This can be done using methods analogous to known methods, for example using an initiator or using UV light. This increases the stability of the vesicles, making them particularly useful in a number of different applications, for example the delivery of substances. Alternatively, vesicle stability can also be increased by cross-linking polymer chains using suitable functional end-groups. It has also been found that cross-linking via the double bonds in the PB block decreases the permeability of vesicles formed from the copolymer, and thus cross-linking provides an easy method of controlling and tailoring the permeability of vesicles.

One preferred embodiment of the invention provides vesicles formed from a block copolymer comprising at least one (poly)2-$C_{1-3}$alkyl-2-oxazoline block and at least one polybutadiene block, said vesicles having transmembrane proteins incorporated into their walls. Such vesicles may be formed by carrying out the vesicle formation process in the presence of transmembrane proteins, especially aquaporins, whereby the transmembrane protein becomes incorporated into the wall of the vesicle. Generally, the process for forming such vesicles is carried out in the presence of a detergent which assists in maintaining the integrity and biological function of the protein. Thus, the above rehydration steps may be carried out using an aqueous solution of a transmembrane protein, preferably also including a detergent. The use of aquaporins is preferred, and aquaporins are robust under a wide range of process conditions. Further details of transmembrane proteins are given in the section "Transmembrane proteins" below Vesicles having transmembrane proteins incorporated therein have utility in the formation of membranes. This is discussed in the section "Membranes" below.

As well as having utility in the formation of membranes, vesicles can be used in other applications. A further use for vesicles according to the invention is in the delivery of substances, for example drugs or cosmetics, and the block copolymers of the invention are particularly suitable for this use because they lead to vesicles with high encapsulation efficiency. In addition, vesicles formed from the copolymers of the present invention have a greater resistance to detergents than vesicles formed from known copolymers, which tend to lose their structure on contact with detergents, making the present invention particularly suitable for delivery of cosmetic agents comprising detergent-like molecules. A wide variety of substances can be contained in the cavity of the vesicles defined by the wall of the vesicle by a number of different routes, for example by adding the substance to the block copolymer during its preparation, by introducing the substance to the block copolymer during vesicle formation, or by treating the vesicles with a solution of the substance until the substance has been absorbed into the vesicles. Amongst substances which may be considered are drugs, cosmetic agents, fragrances, dyes, pigments, photoactive compounds, metal particles, nanoparticles, biological polymers, biological organelles, cell organelles, and chemical reagents. Especially preferred is the use of vesicles in the field of drug or cosmetic delivery, and the invention further provides a vesicle according to the invention containing a drug or a cosmetic agent, specifically containing a drug or a cosmetic agent within the cavity defined by the vesicle wall. A wide variety of drugs or cosmetic agents may be used, for example suitable drugs include small molecule drugs, toxins, cytoxic drugs, genes or RNA, and proteins, for example therapeutic proteins or enzymes.

Because the vesicles according to the invention may be made from copolymers with terminal functional groups, the vesicles may be covalently bonded via these terminal groups to a targeting molecule, for example a binding protein capable of binding to a binding partner on a target, for example an antibody or an antibody fragment. Thus the present invention has utility in the field of targeted drug delivery.

Membranes

The present invention further provides a filtration membrane which comprises a plurality of vesicles according to the present invention having transmembrane proteins incorporated therein. A preferred structure for such a membrane is described in our copending application ref. no. P021889WO claiming priority from UK Application 1405390 of 26 Mar. 2014, which relates to a filtration membrane which comprises a porous support and, covalently bonded to a surface thereof, a layer comprising a plurality of vesicles having transmembrane proteins incorporated therein, said vesicles being formed from an amphiphilic block copolymer; characterised in that within said layer, vesicles are covalently linked together to form a coherent mass. The vesicles of the present invention have particular utility in such membranes. In such membranes, the support carries a layer of vesicles in which multiple vesicles are close packed together. The packing in the layer may for example be hexagonal close packing. The layer of vesicles present on the support surface is thicker than the average diameter of the vesicles, i.e. it is of greater thickness than would be provided by a single layer of vesicles. It is preferred that the layer should have a thickness equivalent to at least 2, for example at least 10, preferably at least 50, more preferably at least 150, and most preferably at least 200, times the average diameter of vesicles. Preferably the layer is not more than 500 times, for example not more than 300 times, the average diameter of a vesicle. So, for example, the layer may have a thickness of from 2 to 500, for example from 50 to 300, especially from 200 to 300 times the average diameter of the vesicles. In absolute terms, the thickness of the vesicle layer is preferably at least 0.04, for example at least 0.1, for example at least 0.2, for example at least 2, preferably at least 10, more preferably at least 30, and most preferably at least 40, microns. There is no particularly preferred maximum thickness for the layer. The layer may for example have a thickness up to 100, for example up to 60, microns. So, for example, the layer may have a thickness of from 0.04 to 100, for example from 0.2 to 100, preferably from 10 to 60, especially from 40 to 60, microns.

To increase robustness, the layer of vesicles in the finished membrane is preferably provided with a protective top coating layer, or a second support layer on the opposite side from the support layer. This top coating may for example provide added protection from mechanical damage during a rolling process. It may for example comprise a hydrophilic polymer, for example polyvinylalcohol.

A filtration membrane of the structure described in our copending application may be prepared by a process which comprises providing an aqueous suspension of vesicles having transmembrane proteins incorporated therein, said vesicles being formed from a block copolymer according to the present invention; depositing said suspension of vesicles on a surface of a porous support; and providing reaction conditions such that covalent bonds are formed between different vesicles and between vesicles and said surface.

Preferably, the filtration membrane is a water filtration membrane, and preferably the transmembrane protein is an aquaporin. Throughout this Specification and claims, unless the context requires otherwise, any reference to a filtration membrane should be understood to include a specific reference to a water filtration membrane, and any reference to a transmembrane protein should be understood to include a specific reference to an aquaporin.

The process for membrane preparation may be carried out in a number of different ways. In a first preferred embodiment, the process comprises:

(a) providing an aqueous suspension of vesicles according to the invention having transmembrane proteins incorporated therein, said vesicles being formed from block copolymers having reactive end groups X;

(b) providing a multifunctional linking agent having at least two reactive groups Y which are reactive with polymer end groups X;

(c) depositing said suspension of vesicles and said multifunctional linker on a support having a surface which is reactive with either polymer end groups X or reactive groups Y; and (d) causing reaction of end groups X with groups Y, and either end groups X or groups Y with the surface of the support.

In a second preferred embodiment, the process comprises:

(a) providing a first aqueous suspension of vesicles according to the invention having transmembrane proteins incorporated therein, said vesicles being formed from block copolymers having reactive end groups X;

(b) providing a second aqueous suspension of vesicles according to the invention having transmembrane proteins incorporated therein, said vesicles being formed from block copolymers having reactive end groups Y which are reactive with polymer end groups X;

(c) depositing said suspensions of vesicles on a support having a surface which is reactive with either polymer end groups X or Y; and (d) causing reaction of end groups X with end groups Y, and either end groups X or end groups Y with the surface of the support.

The above processes result in a physically robust layer of polymer vesicles according to the invention linked to each other, optionally via a linker, and also linked to the surface of the support.

One or both of the block copolymer end groups may be one of the end groups mentioned above. Preferably, one or both of the end groups are groups X which include both an —NH$_2$ and an —NH— group. It is not necessary that all the block copolymer molecules used in the membrane fabrication process should have reactive end groups. The proportion of block copolymer molecules having reactive end groups is not critical, provided that there are sufficient groups to react with reactive groups either in a second population of vesicles or in a multifunctional linker, to form a coherent mass. Generally, at least 10%, for example at least 20%, for example at least 30%, for example at least 40%, for example up to 60%, or up to 100%, of the block copolymer molecules used to form the vesicles will have functional end groups X or Y. Similarly, it is not required that only one type of end group X or Y is present. It may for example be desired to use blends of block copolymers, one containing one reactive end group X(1), for example an end group including an —NH$_2$ group, and the second containing a different reactive end group X(2).

The end groups on any particular block copolymer molecule may be the same as each other, or they may be different. For example, one end group may be a reactive end group X, while the other end group may be a non-reactive group. The exact nature of the groups will of course depend on the nature of the membrane fabrication process and also on the nature of the surface of the support.

Suitable reactive groups include amine groups (reactive with for example carboxylic acid, activated carboxylic acid and/or azide groups), carboxylic acid, activated carboxylic acid and/or azide groups (reactive with for example amine groups Y), and "click chemistry" groups (for example azide or alkyne groups, which are respectively reactive with alkyne and azide groups Y); as well as C=C double bonds present in the PB block. The use of amine groups is particularly preferred.

A wide variety of amine-based end groups is available, and these may contain —NH$_2$ and/or —NH— groups. It has been found that when providing block copolymers containing at least one PAOXA block and at least one PB block with such end groups, the ability of the block copolymer to self-assemble into vesicles is enhanced: this is surprising, as generally it is expected that the properties of amphiphilic block copolymers which most influence vesicle formation are (i) the size and nature of the blocks; and (ii) the polydispersity of the polymer.

When using a multifunctional linking agent, the reactive groups present in that agent may be the same as each other, or they may be different. They must be such as to react with the complementary reactive group present in the vesicles and/or with the surface of the support. Suitable groups are as mentioned above. When using a multifunctional reagent, the reagent may for example contain 3 or 4 reactive groups, but preferably it contains two reactive groups, and any reference herein to a multifunctional reagent should be understood to include a specific reference to a difunctional reagent.

In a preferred embodiment of the invention, the vesicles contain reactive groups which include an amine group; and a complementary reactive group is provided which is an activated carboxylic acid group or an azide, for example a phenylazide, group.

When preparing membranes as described above, the surface of the support may be functionalized in one or more steps to introduce specific reactive groups Z capable of reacting with complementary reactive groups X (i.e. groups including both —NH$_2$ and —NH—) and/or Y. Suitable groups include amine groups (reactive with for example carboxylic acid or activated carboxylic acid groups X and/or Y); carboxylic acid or activated carboxylic acid groups, (reactive with for example amine groups X and/or Y); and "click chemistry" groups (for example azide or alkyne groups reactive with alkyne or azide groups X and/or Y). One example of a multi-step functionalization of a surface is hydrolysis of a polyacrylonitrile surface using acid, e.g. hydrochloric acid, to introduce surface carboxylic acid groups, which may subsequently be activated using 1-ethyl-3-(3-dimethylaminopropyl)carbodiimide (EDC) and N-Hydroxysuccinimide (NHS) followed by conversion into alkyne groups, for example using propargylamine, or into azide groups, for example using amino-triethyleneglycol-azide. However, in another embodiment of the invention, it may not be necessary to functionalise the surface of the support, because X and/or Y may be reactive with groups already present in the material forming the support. For example, Y may be an azide group: such groups are highly reactive once activated using UV light, and are capable of reacting with C—H bonds present in many polymers present in support materials. Specifically, azide, especially phenylazide, groups are capable of covalently bonding with polysulfones, which as discussed below, are a preferred support material for use in the present invention.

Where reference is made to an activated carboxylic acid group, this should be understood to include any conventional activated carboxylic acid group, for example an activated ester such as an N-hydroxysuccinimide ester, or an acid halide. Such activation techniques are well known in the art. In a preferred embodiment, activated carboxylic acid end groups are produced by the reaction of a carboxylic acid group with EDC and NHS. This is a well-known technique often used in the world of protein conjugation and immobilization. The reaction of a carboxyl group with EDC and NHS results in formation of an amine reactive NHS ester.

When using a multifunctional linker, its exact nature is not crucial, provided that it is capable of reacting efficiently to cause linking of the vesicles together by reaction of the X and Y groups.

Suitable multifunctional linkers include homobifunctional crosslinkers, that is, crosslinkers with the same functionalities at both ends. Examples which are capable of binding to amine groups include:
(i) NHS esters. Typical esters include:
   disuccinimidyl glutarate:

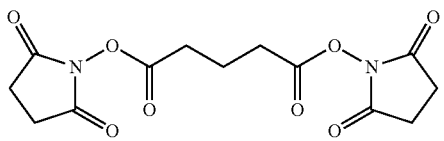 [SMILES: O=C(CCCC(=O)ON1C(=O)CCC1=O)ON1C(=O)CCC1=O]

bis(succinimidyl) polyethylene glycol:

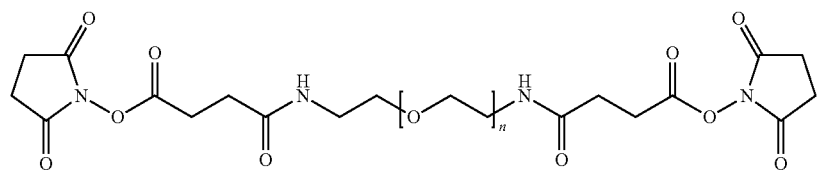

for example bis(succinimidyl) penta(ethylene glycol);
ethylene glycol bis(sulfosuccinimidylsuccinate):

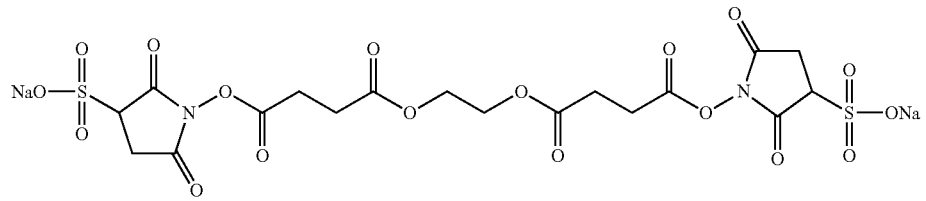

3,3'-dithiobis(sulfosuccinimidylpropionate):

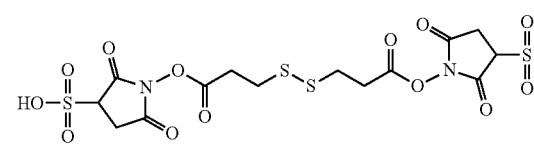

bis(sulfosuccinimidyl)suberate:

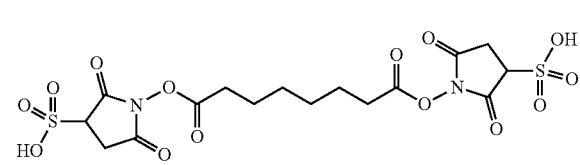 [SMILES: O=C(CCCCCCC(=O)ON1C(=O)CC(S(=O)(=O)O)C1=O)ON1C(=O)CC(S(=O)(=O)O)C1=O]

disuccinimidyl tartrate:

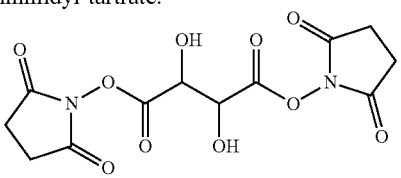

Reagents of this type react with primary amines in slightly alkaline conditions, for example at a pH of 7.2-8.5, for example 7.2-8.0, and yield stable amide bonds. Reaction temperatures are typically in the range of from 0 to 30, for example from 4 to 25° C. The reaction produces N-hydoxysuccinimide which can be removed via dialysis or desalting. The reaction may for example be carried out in PBS buffer at pH 7.2-8.0 for 0.5 to 4 hours at room temp or 4° C.

Sulfo NHS esters contain an —$SO_3$ group on the NHS ring. This has no effect on the chemistry of the reaction, but such reagents tend to have increased water solubility.

(ii) Imidoesters. Typical imidoesters include the following (often obtained as dihydrochloride salts):
   dimethyl adipimidate:

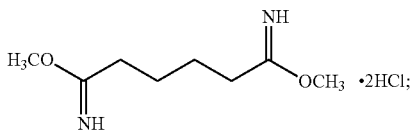 [SMILES: COC(=N)CCCCC(=N)OC]

dimethyl 3,3'-dithiobispropionimidate:

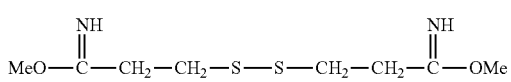

dimethyl suberimidate:

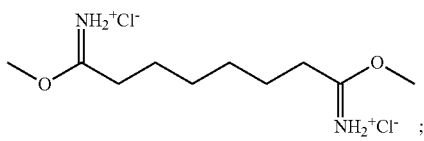

dimethyl pimelimidate:

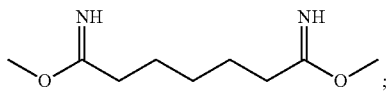

dimethyl adipimidate:

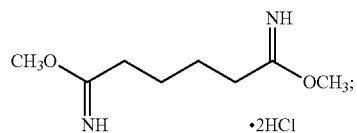

Imidoesters react with primary amines to form amidine bonds. To ensure specificity for primary amines, the reaction is typically carried out in amine-free alkaline conditions (pH 9-11, for example pH10) with borate buffer.

(iii) genipin, which has the formula:

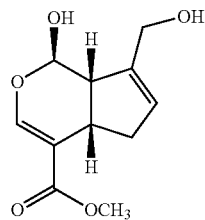 [SMILES: COC(=O)C1=CO[C@@H](O)[C@@H]2C(CO)=CC[C@H]12]

(iv) epoxides, for example triglycidylamine:

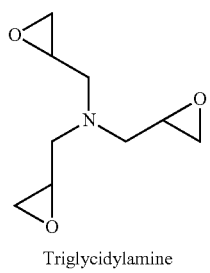 [SMILES: C1OC1CN(CC1CO1)CC1CO1]

Triglycidylamine (v) dialdehyde compounds, for example $HOC.(CH_2)_x.CHO$, where x is 1 to 6. Typical dialdehydes include glutaraldehyde, succindialdehyde, glyoxal, malondialdehyde, and phthalaldehyde.

(vi) COOH-PEG-COOH. This reagent is water-soluble, and if desired may be activated with EDC/NHS to provide reactivity with amines.

Suitable multifunctional linkers also include heterobifunctional crosslinkers, that is, crosslinkers with different functionalities at both ends. Examples include:

1-ethyl-3-(3-dimethylaminopropyl)carbodiimide (usually obtained in the form of the hydrochloride):

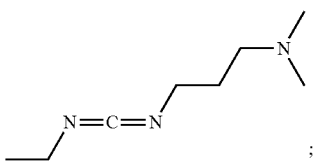

carbitol

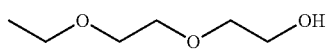

epoxides, for example triglycidalamine;

COOH-PEG-$NH_2$;

sulfosuccinimidyl 6-(4'-azido-2'-nitrophenylamino) hexanoate;

poly(2-hydroxyethyl-co-2-methacryloxyethyl aspartamide);

N,N'-disuccinimidyl carbonate:

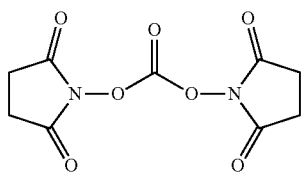 [SMILES: O=C(ON1C(=O)CCC1=O)ON1C(=O)CCC1=O]

p-azidobenzoyl hydrazide:

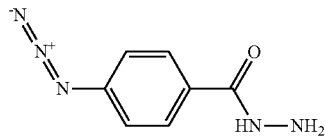

The process for membrane preparation may utilise "click chemistry", which may for example utilise the reaction of an azide with an alkyne. For example, an alkyne group may be introduced as a group Y by reaction of a primary amine with an NHS ester. Many azide-PEG-azide linkers are available commercially.

Preferably a multifunctional linker includes a $(CH_2)_m$ chain in which m is from 2 to 20, preferably from 3 to 10, especially from 3 to 9. An especially preferred difunctional linker is the commercially available product N-sulfosuccinimidyl-6-(4'-azido-2'-nitrophenylamino)hexanoate. This product has the formula:

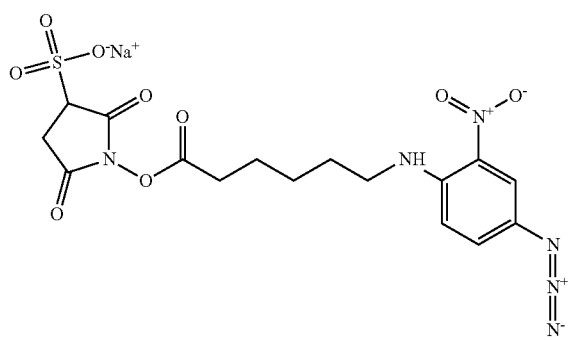

The sulfosuccinimide group is a reactive group Y which is an activated carboxylic acid ester, capable of reacting spontaneously with amine groups. The phenylazide group is a group Y which is inert under light-free conditions, but becomes highly reactive when activated using UV light, reacting readily with amine groups. In the absence of amine groups, the activated group is also capable of reacting with groups of a lower reactivity, even in some circumstances with a C—H bond; specifically, it is capable of reacting with the aromatic C—H groups in a polysulfone.

The conditions under which step (d) of the process for membrane preparation described above, i.e. causing reaction of complementary reactive groups X and Y, and reaction of either X or Y with the surface of the support, is carried out, will of course depend on the nature of the various reactive groups. In some embodiments, the reactive groups will react with each other spontaneously once contacted together under suitable conditions. In other embodiments, photo-activatable groups may be present, in which case the reactants may be contacted together, and subsequently photoirradiated to initiate reaction. In a preferred embodiment, both mechanisms are combined by using a multifunctional reagent having a first group Y which reacts on contact with an end group X, and a second group Y which reacts with an end group X and with the surface of the support on irradiation with UV light.

Thus, the steps of one embodiment of the process may be carried out as follows:
(a) providing an aqueous solution of vesicles according to the invention having transmembrane proteins incorporated therein, said vesicles being formed from a block copolymer having reactive end groups X;
(b) providing an multifunctional, preferably difunctional, linking agent having at least two reactive groups Y which are reactive with polymer end groups X, including a first reactive group Y(1) being capable of reaction with polymer end groups X under a first set of reaction conditions, and a second reactive group Y(2) which is unreactive with polymer end groups X under said first set of reaction conditions but which is reactive with polymer end groups X under a second set of reaction conditions;
(b') mixing said aqueous solution of vesicles with said multifunctional linking agent under said first set of reaction conditions so that reactive group Y(1) reacts with polymer end groups X;
(c) depositing the resulting solution on a support which is reactive with second reactive group Y(2), in an amount sufficient to produce the desired layer of vesicles; and
(d) causing reaction of end groups X with said second reactive group Y(2), and second reactive end groups Y(2) with the surface of the support, by applying said second set of reaction conditions.

Any suitable reaction conditions which differentiate the two reaction steps may be used. For example, the first set of reaction conditions may involve groups X and Y(1) which react at a first temperature while the second set of reaction conditions may involve groups X and Y(2) which react at a second, higher, temperature. However, in a preferred embodiment, X and Y(1) are such that they react spontaneously on contact, or with heating if necessary, while X and Y(2) are such that they react only when activated by photoirradiation. Accordingly, a particularly preferred process comprises:
(a) providing an aqueous solution of vesicles according to the invention having transmembrane proteins incorporated therein, said vesicles being formed from a block copolymer having reactive end groups X;
(b) providing an multifunctional, preferably difunctional, linking agent having at least two reactive groups Y which are reactive with polymer end groups X, including a first reactive group Y(1) being capable of reaction with polymer end groups X on contact, and a second reactive group Y(2) being capable of reaction with polymer end groups X on photoirradiation;
(b') mixing said aqueous solution of vesicles with said multifunctional linking agent under conditions such that said first reactive group Y(2) reacts with polymer end groups X;
(c) depositing the resulting solution on a support which is reactive with second reactive group Y(2), in an amount sufficient to produce the desired layer of vesicles; and
(d) applying photoirradiation to cause reaction of end groups X with said second reactive group Y(2), and second reactive end groups Y(2) with the surface of the support.

In all the above embodiments, the amount of suspension deposited in step (c) is sufficient to provide the surface of the support with a continuous layer of vesicles. Generally, after step (d) has been carried out, this layer will be in the form of a coherent mass which has a thickness greater than the average diameter of the vesicles; or, in absolute terms, has a thickness of at least 0.01 microns, especially 0.04 microns.

A very wide range of reaction conditions may be used to effect the above processes. In one embodiment, when using a multifunctional linker, the quantity of multifunctional linker used will be such that the total quantity of reactive groups Y present is in excess of the total quantity of polymer end groups X present to ensure adequate crosslinking. Control of pH, temperature and other reaction conditions is conventional and within the normal practice of the skilled man.

Overall, the use of vesicles according to the invention together with a complementary multifunctional linking agent gives major advantages compared with known processes for the preparation of working filtration membranes.

The support may be made of any suitable microporous material. It may for example be based upon a conventional membrane support, as used in reverse osmosis or ultrafiltration membranes. Such supports may for example be made from a polyolefin, cellulose, regenerated cellulose, cellulose acetate, polyacrylonitrile, polyethersulfone, or polysulfone. In a preferred embodiment of the invention, the support is made from a polysulfone.

Chemical functionality of the support membrane may be delivered in the form of additives, which may be either low molecular weight or polymeric, to the casting dope, or functionalization of the support surface, for example by chemical treatments, graft polymerisation or plasma polymerization. By these means, the following chemical transformations of the support may for example be accomplished: conversion of amine groups into carboxylic acid groups, or vice versa; conversion of aldehydes into amines; and conversion of hydroxyl groups into carboxylic acid groups. All such reactions are well known in the art.

Porous ultrafiltration membranes may for example be prepared by air casting, where the dissolved polymer solution passes under a series of air flow ducts that control the evaporation of the solvents in a very slow manner; solvent or emersion casting, where the dissolved polymer is spread onto a moving belt and run through a bath of liquid, and the liquid in the bath exchanges with the solvent in the lacquer and causes the formation of the pores; thermal casting, where heat is used to drive the solubility of the polymer in a given solvent system. The lacquer is then cast out onto a moving belt that is being cooled. Quenching the heat in the lacquer causes precipitation to start and the pores to form. Materials typically used in the process include but are not limited to cellulose regenerated, cellulose nitrate, cellulose acetate, polyamide, polysulfone, poly(ether sulfone), polycarbonate, poly(ether imide), poly(2,6-dimethyl-1,4-phenylene oxide), polyimide, poly(vinylidene fluoride), polytetrafluoroethylene, polypropylene, polyacrylonitrile, poly (methyl methacrylate, polyvinyl alcohol, and polydimethylsiloxane. The morphology of the cast is regulated by the configuration of the final module. It may for example comprise a flat-sheet for spiral wound elements; hollow-fibre for hollow-fibre elements; or it may be tubular.

Preparation of a membrane having a layer comprising a coherent mass of vesicles, said layer having a defined thickness, may be achieved by control of the concentration of vesicles present in the solution of vesicles applied to the support and/or by the volume of solution deposited on the support.

The advantage of the membranes of the present invention is that any possible pathway through the membrane other than through the transmembrane proteins embedded in the walls of the polymer vesicles, is minimised, while providing a large number of possible transmembrane proteins per unit surface area of the support membrane, thus maximising flux through the membrane. The process for preparing the membranes is technically simple, and the resulting membranes are physically robust.

Transmembrane Proteins

Vesicles and membranes according to the invention may contain transmembrane proteins. Aquaporins are biological cell transmembrane proteins whose function is to selectively transport water and no other molecules; the transport channel of the protein is a two-way channel through which water can flow in either direction. They are expressed by many human cell types, and also by bacterial and plant cells. Any of the different members of the aquaporin family of proteins can be used in the present invention. Suitable aquaporins include Aqp 4, Aqp 1 and, especially, Aqp Z. Aquaporins may exist in monomeric, dimeric, tetrameric and higher oligomeric forms, as well as mutated, conjugated and truncated versions of the primary sequence. Provided that the biological function of the aquaporin, i.e. the selective transport of water, is maintained, any of these may be used in membranes formed from block copolymers according to the present invention.

Any other transmembrane protein having desirable transport properties may be used in the present invention. Variants of such transmembrane proteins, including naturally or non-naturally occurring variants and orthologs or paralogs of such proteins may be used. Such proteins include for example:

Monotopic Membrane Proteins
  Cyclooxygenases
    Ram Prostaglandin H2 synthase-1 (cyclooxygenase-1 or COX-1): *Ovis aries*
    Ram Prostaglandin H2 synthase-1 (COX-1) R120Q/ Native Heterodimer: *Ovis aries*
    Aspirin Acetylated COX-1
    Cyclooxygenase-2: *Mus Musculus*
  Squalene-Hopene Cyclases
    Squalene-hopene cyclase: *Alicyclobacillus acidocaldarius*
  Monoamine Oxidases
    Monoamine Oxidase B: Human mitochondrial outer membrane
    Monoamine Oxidase A: Rat mitochondrial outer membrane
    Monoamine Oxidase A: Human mitochondrial outer membrane
    G110A mutant
  Hydrolases
    Fatty acid amide hydrolase: *Rattus norvegicus*
  Oxidoreductases (Monotopic)
    Sulfide:quinone oxidoreductase in complex with decylubiquinone: *Aquifex aeolicus*
    Electron Transfer Flavoprotein-ubiquinone oxidoreductase (ETF-QO): *Sus scrofa*
  Peptidoglycan Glycosyltransferases
    Peptidoglycan Glycosyltransferase: *Staphylococccus aureus*
    Peptidoglycan Glycosyltransferase penicillin-binding protein 1a (PBP1a): *Aquifex aeolicus*
    Peptidoglycan Glycosyltransferase penicillin-binding protein 1b (PBP1b): *Escherichia coli*
  Peptidases
    Signal Peptidase (SPase): *Escherichia coli*
    Signal Peptide Peptidase (SppA), native protein: *Eschericia coli*
  Dehydrogenases
    Glycerol-3-phosphate dehydrogenase (GlpD, native): *Escherichia coli*
  Dihydroorotate Dehydrogenases (DHODH, class 2)
    Dihydroorotate Dehydrogenase: *Escherichia coli*
    Dihydroorotate Dehydrogenase: *Rattus rattus*
    Dihydroorotate Dehydrogenase, apo form: *Homo sapiens*
    Dihydroorotate Dehydrogenase: *Plasmodium falciparum:* 3d7
  Polymerases
    TagF teichoic acid polymerase: *Staphylococcus epidermidis*
  ADP-Ribosylation Factors
    ADP-ribosylation factor (ARF1), myristoylated: *Saccharomyces cerevisiae*
    ADP-ribosylation factor (ARF1*GTP), myristoylated: *Saccharomyces cerevisiae*
  Isomerases
    RPE65 visual cycle retinoid isomerase: *Bos Taurus*
Transmembrane Proteins: Beta-Barrel
  Beta-Barrel Membrane Proteins: Multimeric
    Porin: *Rhodobacter capsulatus*
    Porin: *Rhodopeudomonas blastica*
    OmpK36 osmoporin: *Klebsiella pneumonia*
    Omp32 anion-selective porin: *Comamonas acidovorans*
    Omp32 anion-selective porin: *Delftia acidovorans*
    OmpF Matrix Porin: *Escherichia coli*
    OmpC Osmoporin: *Escherichia coli*

OmpG *monomeric* porin: *Escherichia coli*
PhoE: *Escherihia coli*
LamB Maltoporin: *Salmonella typhimurium*
LamB Maltoporin: *Escherichia coli*
LamB Maltoporin: *Escherichia coli*
ScrY sucrose-specific porin: *Salmonella typhimurium*
MspA mycobacterial porin: *Mycobacterium smegmatis*
OprP phosphate-specific transporter: *Pseudomonas aeruginosa*
OprD basic amino acid uptake channel: *Pseudomonas aeruginosa*
OpdK hydrocarbon transporter: *Pseudomonas aeruginosa*
PorB outer membrane protein, native structure: *Neisseria meningitidis*

Beta-Barrel Membrane Proteins: Monomeric/Dimeric
TolC outer membrane protein: *Escherichia coli*
TolC outer membrane protein, ligand blocked: *Escherichia coli*
TolC outer membrane protein (Y362F, R367E): *Escherichia coli*
  C2 Form
  P2:2:2 form
VceC outer membrane protein: *Vibrio cholera*
OprM drug discharge outer membrane protein: *Pseudomonas aeruginosa*
CusC heavy metal discharge outer membrane protein: *Escherichia coli*
CusBA heavy-metal efflux complex outer membrane protein: *Escherichia coli*
BenF-like Porin (putative): *Pseudomonas fluorescens*
OprM drug discharge outer membrane protein: *Pseudomonas aeruginosa*
apo BtuB cobalamin transporter: *Escherichia coli*
BtuB: *Escherichia coli*
apo BtuB by in meso crystallization: *Escherichia coli*
Colicin I receptor: *Escherichia coli*
OmpA: *Escherichia coli*, 2.5 Å
OmpA with four shortened loops: *Escherichia coli* Called β-barrel platform (BBP)
OmpT outer membrane protease: *Escherichia coli*
Pla Plasminogen activator (native 1): *Yersinia pestis*
OmpW outer membrane protein: *Escherichia coli*
  Orthorhomibic Form
  Trigonal Form
OprG outer membrane protein: *Pseudomonas aeruginosa*
OmpX: *Escherichia coli*
TtoA Outer Membrane Protein (OMP): *Thermus thermophilus* HB27
OmpLA (PldA) outer membrane phospholipase A monomer: *Escherichia coli*
OmpLA (PldA) active-site mutant (N156A): *Escherichia coli*
OpcA adhesin protein: *Neisseria meningitidis*
NspA surface protein: *Neisseria meningitides*
NalP autotransporter translocator domain: *Neisseria meningitides*
NanC Porin, model for KdgM porin family: *Escherichia coli*
Hia1022-1098 trimeric autotransporter: *Haemophilus influenza*
  Hia992-1098
EspP autotransporter, postcleavage state: *Escherichia coli*
EstA Autotransporter, full length: *Pseudomonas aeruginosa*
PagP outer membrane palimitoyl transferease: *Escherichia coli*
FadL long-chain fatty acid transporter: *Escherichia coli*
FadL long-chain fatty acid transporter A77E/S100R mutant: *Escherichia coli*
  ΔS3 kink
  P34A mutant
  N33A mutant
  ΔNPA mutant
  G212E mutant
FadL homologue long-chain fatty acid transporter: *Pseudomonas aeruginosa*
FauA alcaligin outer membrane transporter: *Bordetella pertusssis* TodX hydrocarbon transporter: *Pseudomonas putida*
TbuX hydrocarbon transporter: *Ralstonia pickettii*
Tsx nucleoside transporter (apoprotein): *Eschericia coli*
FhuA, Ferrichrome-iron receptor: *Escherichia coli*
FepA, Ferric enterobactin receptor: *Escherichia coli*
FecA, siderophore transporter: *Escherichia coli*
HasR heme-uptake receptor: *Serratia marcescens*
  Ile671Gly mutant
FptA, pyochelin outer membrane receptor: *Pseudomonas aeruginosa*
FpvA, Pyoverdine receptor: *Pseudomonas aeruginosa*
FpvA, Pyoverdine receptor (apo form): *Pseudomonas aeruginosa*
P pilus usher translocation domain, PapC130-640: *Escherichia coli*

Beta-Barrel Membrane Proteins: Mitochondrial Outer Membrane
VDAC-1 voltage dependent anion channel: Human
VDAC-1 voltage dependent anion channel: Murine Omp85-TpsB Outer Membrane Transporter Superfamily
FhaC Filamentous Hemagglutinin Transporter: *Bordetella pertussis*
TeOmp85-N POTRA domains: *Thermosynechococcus* anaOmp85-N *Anabaena* sp. PCC7120
BamA: *Escherichia coli*
BamE: *Escherichia coli*

Non-constitutive. Beta-sheet Pore-forming Toxins
Alpha-hemolysin: *Staphylococcus aureus*
LukF: *Staphylococcus aureus*
Perfringolysin O (PFO) protomer: *Clostridium perfringens*
Anthrax Protective Antigen (PA) and Lethal Factor (LF) Prechannel Complex: *Bacillus anthraciss*
Lymphocyte preforin monomer: *Mus musculus*

Transmembrane Proteins: Alpha-Helical
Non-constitutive. Alpha-helical Pore-forming Toxins.
  Cytolysin A (ClyA, aka HlyE): *Escherichia coli*
  FraC eukaryotic pore-forming toxin from sea anemone: *Actinia fragacea*
Outer Membrane Proteins
  Wza translocon for capsular polysaccharides: *Escherichia coli*
  Porin B monomer: *Corynebacterium glutamicum*
  Type IV outer membrane secretion complex: *Escherichia coli*

Bacteriorhodopsin (BR): *Halobacterium salinarium*
Halorhodopsin (HR): *Halobacterium salinarium*
Halorhodopsin (HR): *Natronomonas pharaonis*
Sensory Rhodopsin I (SRI): *Anabaena* (*Nostoc*) sp. PCC7120
Sensory Rhodopsin II (SRII): *Natronomonas pharaonis*
Archaerhodopsin-1 (aR-1): *Halorubrum* sp. aus-1
Archaerhodopsin-2 (aR-2): *Haloroubrum* sp. aus-2
Xanthorhodopsin: *Salinibacter ruber*
G Protein-Coupled Receptors (GPCRs)
    Rhodopsin: Bovine Rod Outer Segment (*Bos Taurus*)
    Rhodopsin: Squid (*Todarodes pacificus*)
    β1 adrenergic receptor (engineered): *Meleagris gallopavo* (turkey)
    β2 adrenergic receptor: *Homo sapiens*
    Methylated 32 adrenergic receptor: *Homo sapiens*
    A2A adenosine receptor: *Homo sapiens*
    CXCR4 Chemokine Receptor: *Homo sapiens*
    Dopamine D3 Receptor: *Homo sapiens*
Autonomously Folding "Membrane Proteins" (Sec-independent)
    Mistic membrane-integrating protein: *Bacillus subtilis*
Glycoproteins
    Glycophorin A transmembrane-domain dimer: *Homo sapiens*
SNARE Protein Family
    Syntaxin 1A/SNAP-25/Synaptobrevin-2 Complex: *ratus ratus*
Integrin Adhesion Receptors
    Human Integrin αIIbβ3 transmembrane-cytoplasmic heterodimer: *Homo sapiens*
Histidine Kinase Receptors
    ArcB (1-115) Aerobic Respiration Control sensor membrane domain: *Escherichia coli*
    QseC (1-185) Sensor protein membrane domain: *Escherichia coli*
    KdpD (397-502) Sensor protein membrane domain: *Escherichia coli*
Immune Receptors
    Transmembrane ζ-ζ dimer of the TCR-CD3 complex: *Homo sapiens*
    DAP12 dimeric: *Homo sapiens*
Channels: Potassium and Sodium Ion-Selective
    KcsA Potassium channel, H+ gated: *Streptomyces lividans*
    KcsA Potassium channel E71H-F103A inactivated-state mutant (closed state): *Streptomyces lividans*
    KcsA Potassium channel E71I modal-gating mutant: *Streptomyces lividans*
    KvAP Voltage-gated potassium Channel: *Aeropyrum pernix*
    Kv1.2 Voltage-gated potassium Channel: *Rattus norvegicus*
    Kv1.2/Kv2.1 Voltage-gated potassium channel chimera: *Rattus norvegicus*
    F233W Mutant
    MthK Potassium channel, Ca++ gated: *Methanothermobacter thermautotrophicus*
    Human BK Channel Ca2+-activation apparatus: *Homo sapiens*
    Kir3.1-Prokaryotic Kir Chimera: *Mus musculus* & *Burkholderia xenovornas*
    Kir2.2 Inward-Rectifier Potassium Channel: *Gallus gallus*
    KirBac1.1 Inward-Rectifier Potassium channel: *Burkholderia pseudomallei*
    MlotiK1 cyclic nucleotide-regulated K+-channel: *Mesorhizobium loti*
    mGIRK1 G-Protein Gated Inward Rectifying Potassium Channel: *Mus musculus*
    NaK channel (Na+complex): *Bacillus cereus*
    D66/S70E Mutant
    D66N Mutant
    D66E Mutant
    CNG-mimicking NaK channel mutant: *Bacillus cereus*
    NaK channel; K+ selective mutant: *Bacillus cereus*
Channels: Other Ion Channels
    GluA2 Glutamate receptor (AMPA-subtype): *Rattus norvegicus*
    M2 proton channel: Influenza A
    M2 proton channel: Influenza B
    ASIC1 Acid-Sensing Ion Channel: *Gallus gallus*
    ATP-gated P2X4 ion channel (apo protein): *Danio rerio* (zebra fish)
    Nicotinic Acetylcholine Receptor Pore: *Torpedo marmorata*
    Prokaryotic pentameric ligand-gated ion channel (pLGIC): *Erwinia chrysanthemi*
    Prokaryotic pentameric ligand-gated ion channel (GLIC): *Gloebacter violaceus*
    E221A mutant
    Prokaryotic pentameric ligand-gated ion channel (GLIC), wildtype-TBSb complex: *Gloebacter violaceus*
    Wildtype-TEAs complex
    E221D-TEAs complex
    Wildtype-TMAs complex
    Wildtype-bromo-lidocaine complex
    Wildtype-Cd2+ complex
    Wildtype-Zn2+ complex
    Wildtype-Cs+ complex
    MscL Mechanosensitive channel: *Mycobacterium tuberculosis*
    MscS voltage-modulated mechanosensitive channel: *Escherichia coli*
    CorA Mg2+ Transporter: *Thermotoga maritime*
    MgtE Mg2+ Transporter: *Thermus thermophilus*
    SLAC1 anion channel, TehA homolog (wild-type): *Haemophilus influenzae*
    F262A mutant
    F262L mutant
    F262V mutant
    G15D mutant
Channels: Protein-Conducting
    SecYEβ protein-conducting channel: *Methanococcus jannaschii*
Channels: Aquaporins and Glyceroporins
    AQP0 aquaporin water channel: *Bovine lens*
    AQP1 aquaporin water channel: Human red blood cell
    AQP1 aquaporin water channel: Bovine red blood cell
    AQP4 aquaporin water channel: rat glial cells
    S180D Mutant
    AQP4 aquaporin water channel: Human
    AQP5 aquaporin water channel (HsAQP5): human
    AqpM aquaporin water channel: *Methanothermobacter marburgensis*
    AqpZ aquaporin water channel: *Escherichia coli*

AqpZ aquaporin (C9S/C20S), T183C mutant: *Escherichia coli*
   L170C Mutant
AqpZ aquaporin mutant F43W: *Escherichia coli*
   H17G/T183F Mutant
   F43WH174G/T183F Mutant
SoPIP2;1 plant aquaporin: *Spinacia oleracea*
GlpF glycerol facilitator channel: *Escherichia coli*
GlpF glycerol facilitator channel, W84F/F200T-mutant: *Escherichia coli*
PfAQP aquaglyceroporin: *Plasmodium falciparum*:
Aqy1 yeast aquaporin (pH 3.5): *Pischia pastoris*
Channels: Formate Nitrate Transporter (FNT) Family
   FocA, pentameric aquaporin-like formate transporter: *Escherichia coli*
   FocA formate transporter without formate: *Vibrio cholerae*
   FocA formate transporter: *Salmonela typhimurium*
Channels: Urea Transporters
   Urea transporter: *Desulfovibrio vulgaris*
   Connexin 26 (Cx26; GJB2) gap junction: Human
Channels: Amt/Rh proteins
   AmtB ammonia channel (mutant): *Escherichia coli*
   AmtB ammonia channel (wild-type): *Escherichia coli*
     H168E Mutant
     H168A Mutant
     H168F Mutant
     H318A Mutant
     H318 Mutant
     H318F Mutant
     H168A/H318A Mutant
   Amt-1 ammonium channel: *Archaeoglobus fulgidus*
   Rh protein, possible ammonia or CO2 channel: *Nitrosomonas europaea*
   Human Rh C glycoprotein ammonia transporter: *Homo sapiens*
Intramembrane Proteases
   GlpG rhomboid-family intramembrane protease: *Eschericia coli*
     W136A Mutant
     S201T Active-Site Mutant
   GlpG rhomboid-family intramembrane peptidase: *Haemophilus influenzae*
   Site-2 Protease (S2P). Intramembrane Metalloprotease: *Methanocaldococcus jannaschii*
   Signal Peptide Peptidase (SppA), native protein: *Escherichia coli*
Membrane-Bound Metalloproteases
   apo-FtsH ATP-dependent metalloprotease: *Thermotoga maritima*
H+/Cl− Exchange Transporters
   H+/Cl− Exchange Transporter: *Salmonella typhimurium*
   H+/Cl− Exchange Transporter: *Escherichia coli*
     E148A Mutant
     E148Q Mutant
     S107A/E148Q/445A Mutant
   Monomeric H+/Cl− Exchange Transporter: *Escherichia coli*
   +/Cl− Eukaryotic Exchange Transporter: *Cyanidioschyzon merolae*
   H+/Cl− Eukaryotic Exchange Transporter: *Synechocystis* sp. pcc 6803
Bacterial Mercury Detoxification Proteins
   MerF Hg(II) transporter: *Morganella morganii*
Multi-Drug Efflux Transporters
   AcrB bacterial multi-drug efflux transporter: *Escherichia coli*
   AcrB bacterial multi-drug efflux transporter, apo protein, N109A mutant: *Escherichia coli*
   AcrB bacterial multi-drug efflux transporter, D407A mutant: *Escherichia coli*
   MexB bacterial multi-drug efflux transporter: *Pseudomonas aeruginosa*
   CusA metal-ion efflux pump: *Escherichia coli*
   EmrE bacterial multi-drug efflux transporter: *Escherichia coli*
   NorM Multidrug and Toxin Compound Extrusion (MATE) transporter (apo form): *Vibrio cholerae*
Membrane-Associated Proteins in Eicosanoid and Glutathione Metabolism (MAPEG)
   Microsomal Prostaglandin E Synthase 1: Human
   5-Lipoxygenase-Activating Protein (FLAP) with Bound MK-591 Inhibitor: Human
   Leukotriene LTC4 Synthase: Human
Major Facilitator Superfamily (MFS) Transporters
   LacY Lactose Permease Transporter (C154G mutant): *Escherichia coli*
   LacY Lactose Permease (wild-type) with TDG: *Escherichia coli*
   FucP Fucose Transporter in outward-facing conformation: *Escherichia coli*
     N162A Mutant
   GlpT Glycerol-3-Phosphate Transporter: *Escherichia coli*
   EmrD Multidrug Transporter: *Escherichia coli*
   PepTSo Oligopeptide-proton symporter: *Shewanella oneidensis*
Solute Sodium Symporter (SSS) Family
   vSGLT Sodium Galactose Transporter: *Vibrio parahaemolyticus*
     K294A Mutant
Nucleobase-Cation-Symport-1 (NCS1) Family
   Mhp1 Benzyl-hydantoin transporter: *Microbacterium liquefaciens*
Betaine/Choline/Carnitine Transporter (BCCT) Family
   BetP glycine betaine transporter: *Corynebacterium glutamicum*
   CaiT carnitine transporter: *Escherichia coli*
   CaiT carnitine transporter: *Proteus mirabilis*
Amino Acid/Polyamine/Organocationi (APC) Superfamily
   AdiC Arginine:Agmatine Antiporter: *Escherichia coli*
     N22A, L123W Mutant
     N101A Mutant
   apo ApcT Na+-independent Amino Acid Transporter: *Methanocaldococcus jannaschii*
Amino Acid Secondary Transporters
   LeuTAa Leucine transporter: *Aquifex aeolicus*
   Wild-type LeuT transporter: *Aquifex aeolicus*
     E290S Mutant
   Mutant LeuT transporter with Nitroxide Spin Label (F177R1): *Aquifex aeolicus*
     I1204R1 Mutant
   Glutamate Transporter Homologue (GltPh): *Pyrococcus horikoshii*
   Aspartate Transporter Li+-Bound State(GltPh): *Pyrococcus horikoshii*
Cation Diffusion Facilitator (CDF) Family
   YiiP Zinc Transporter: *Escherichia coli*
Antiporters
   NhaA Na+/H+ antiporter: *Escherichia coli*

Mitochondrial ADP/ATP Carrier: Bovine heart mitochondria

Energy-Coupling Factor (ECF) Transporters
  RibU, S Component of the Riboflavin Transporter: *Staphylococcus aureus*

ATP Binding Cassette (ABC) Transporters
  BtuCD Vitamin B12 Transporter: *Escherichia coli*
  Sav1866 Multidrug Transporter: *Staphylococcus aureus*
  Molybdate Transporter ModB2C2: *Archaeoglobus fulgidus*
  ModBC Molybdate ABC Transporter: *Methanosarcina acetivorans*
  HI1470/1 Putative Metal-Chelate-type ABC Transporter: *Haemophilus influenza*
  MsbA Lipid "flippase" with bound AMPPNP: *Salmonella typhimurium*
  P-Glycoprotein: *Mus musculus* (mouse)
  MalFGK2-MBP Maltose uptake transporter complex: *Escherichia coli*
  MetNI Methionine uptake transporter complex: *Escherichia coli*
  FbpC ferric iron-uptake transporter nucleotide-binding domain: *Neisseria gonorrhoeae*

Superfamily of K+ Transporters (SKT proteins)
  TrkH potassium ion transporter: *Vibrio parahaemolyticus*
  Calcium ATPase: Rabbit sarcoplasmic reticulum
  Na,K-ATPase: Pig Kidney
  Na,K-ATPase: Shark
  Na,K-ATPase Regulatory Protein FXYD1: Human
  Phospholamban homopentamer: Human sarcoplasmic reticulum
  Plasma Membrane H+-ATPase: *Arabidopsis thaliana*

V-type ATPase
  Rotor of V-type Na+-ATPase: *Enterococcus hirae*
  V1-ATPase Complex: *Thermus thermophiles*
  A3B3 complex of V1-ATPase: *Thermus thermophilus*

F-type ATPase
  F1-ATPase from bovine heart mitochondria: *Bos Taurus*
  ATP synthase (F1c10): *S. cerevisiae*
  F1 ATPase: *S. cerevisiae*
  Rotor (c11) of Na+-dependent F-ATP Synthase: *Ilyobacter tartaricus*
  Rotor (c14) of H+-dependent F-ATP Synthase of spinach chloroplasts: *Spinacia oleracea*
  Rotor (c15) of H+-dependent F-ATP Synthase of an alkaliphilic cyanobacterium: *Spirulina platensis*
  Rotor (c13) of H+-dependent F-ATP Synthase: *Bacillus pseudofirmus*
  Peripheral stalk of H+-dependent F-ATP Synthase: *Thermus thermophilus*

Phosphotransferases
  Diacylglycerol kinase (DAGK): *Escherichia coli*

Hydrolases
  Estrone Sulfatase: Human placenta

Oxygenases
  Particulate methane monooxygenase (pMMO): *Methylococcus capsulatus*
  Particulate methane monooxygenase (pMMO): *Methylosinus trichosporium* OB3b Oxidoreductases
  Sulfide:quinone oxidoreductase: *Aquifex aeolicus*
  Electron Transfer Flavoprotein-ubiquinone oxidoreductase (ETF-QO): *Sus scrofa*
  Glycerol-3-phosphate dehydrogenase (GlpD, native): *Escherichia coli*
  NarGHI Nitrate Reductase A: *Escherichia coli*
    K86A Mutant
    H66Y Mutant
  NrfH Cytochrome C Quinol Dehydrogenase: *Desulfovibrio vulgaris*
  DsbB-DsbA Periplasmic Oxidase Complex: *E. coli*
  DsbB-Fab complex: *Eschericia coli*
  wtDsbB-DsbA(Cys133A)-Q8 Complex: *E. coli*
  Vitamin K epoxide reductase: *Synechococcus* sp.

Mo/W bis-MGD Oxidoreductases
  Polysulfide Reductase PsrABC (native): *Thermus thermophiles*

Electron Transport Chain Complexes: Complex I
  Complex I membrane domain: *Escherichia coli*
  Complex I complete: *Thermus thermophiles*

Electron Transport Chain Complexes: Complex II
  Native Fumarate Reductase Complex: *Escherichia coli*
  Fumarate Reductase Complex: *Wolinella succinogenes*
  Formate dehydrogenase-N: *Escherichia coli*
  Succinate dehydrogenase (Complex II): *Escherichia coli*
  Succinate:ubiquinone oxidoreductase (SQR, Complex II): porcine heart mitochondria
  Succinate:ubiquinone oxidoreductase (SQR, Complex II): chicken heart mitochondria Electron Transport Chain Complexes: Complex III (Cytochrome bc1)
  Cytochrome bc1: *Bos Taurus*
  Cytochrome bc1: *Gallus gallus*
  Cytochrome bc1: *Sarcomyces cerevisiae*
  Cytochrome bc1: *Rhodobacter Sphaeroides*

Electron Transport Chain Complexes: Cytochrome b6f of Oxygenic Photosynthesis
  Cytochrome b6f complex: *Mastigocladus laminosus*
  Cytochrome b6f complex: *Chlamydomonas reinhardtii*
  Cytochrome b6f complex: *Nostoc* sp. PCC 7120

Electron Transport Chain Complexes: Complex IV (Cytochrome C Oxidase)
  Cytochrome C Oxidase, aa3: *Bos taurus* (bovine) heart mitochondria
  Cytochrome C Oxidase, aa3: *Paracoccus denitrificans*
    N131D Variant
  Cytochrome Oxidase, cbb3: *Pseudomonas stutzeri*
  Cytochrome ba3: *Thermus thermophilus*
  Cytochrome C Oxidase wild-type: *Rhodobacter sphaeroides*
  Ubiquinol Oxidase, cytochrome bo3: *E. coli*

Nitric Oxide Reductases
  Nitric Oxide Reductase: *Pseudomonas aeruginosa*

Photosystems
  Photosystem I: *Thermosynechococcus elongates*
  Photosystem I (plant): *Psium sativum*
  Photosystem II: *Thermosynechococcus elongates*
  Photosystem II: *Thermocynechococcus vulcanus*

Light-Harvesting Complexes
  Light-Harvesting Complex: *Rhodopseudomonas acidophila*
  Light-Harvesting Complex: *Rhodospirillum molischianum*

Light-Harvesting Complex LHC-II, Spinach Photosystem II: *Spinacia oleracia*
Light-Harvesting Complex CP29, Spinach Photosystem II: *Spinacia oleracia*
Light-Harvesting Complex LHC-II, Pea Photosystem II: *Pisum sativum*
Photosynthetic Reaction Centers
Photosynthetic Reaction Center: *Blastochloris viridis*
Photosynthetic Reaction Center: *Rhodobacter sphaeroides*
Photosynthetic Reaction Center: *Thermochromatium tepidum*

Figure 1A:
FIGS. 1A and 1B show LSM imaging micrographs of vesicles according to the invention.

The following Examples illustrate the invention.

EXAMPLE 1: POLYMER PREPARATION

Step (a): PB Synthesis

Polybutadiene was synthesized following the protocol of Hillmyer, M. A.; Bates, F. S. 1996, 9297, 6994-7002 with some modifications. The anionic polymerization of butadiene was carried out in THF at −60 to −50° C. using sec-butyl-butyllithium as the initiator. A dry 2 neck flask was dried in the oven overnight and a line was attached to one port with a septum to another. The flask was flame dried and a stir bar was added. 30 ml of Dry Solv THF was added to the 2 neck flask using a cannula. 11 ml butadiene (0.13 mol) was condensed in a condensing flask. Liquid nitrogen was first used to condense polybutadiene and then melted using a dry ice-acetone bath. This was transferred to the 2 neck flask using a cannula. 7 ml (0.0098 moles) of 1.4 M sec-butyl lithium initiator was swiftly added. The polymerization was allowed to proceed for 3 h. End capping was accomplished by adding 2 ml (0.051 moles) of ethylene oxide at −60° C. upon complete conversion of the butadiene. Acidic methanol (5 ml HCl:50 ml methanol) was then used to liberate the polybutadiene alcohol which was isolated by evaporation of the solvent. Inorganic salts were removed by extraction of a cyclohexane solution of the polymer with distilled water. Polymer was left on high vacuum to remove water. Further drying was achieved by refluxing the polymer in dry hexane using molecular sieves in soxhlet extractor.

Step (b): PB-PMOXA Synthesis 20 g (0.0260M) of polybutadiene (Mn 769 g/mol) were functionalized with 7.33 g (0.0260M) triflic acid anhydride (SigmaAldrich 176176-5G) in the presence of 2.63 g (0.0260M) of triethylamine (SigmaAldrich T0886) at −10 deg C. under argon. Organic salts were further filtered out. Triflate-functionalized PB served as a macro-initiator of cationic ring opening polymerization of 2-methyl-2-oxazoline (SigmaAldrich 137448).

Polymerisation was allowed to proceed in anhydrous ethyl acetate (SigmaAldrich 270989) at 40 deg C. for 12 h. Reaction was terminated with ethylene diamine 0.4 g (SigmaAldrich 03550). This provided primary- and secondary-amine terminated PB-PMOXA polymer.

Polymer Characterization:

$PB_{12}$—OH

NMR 5.45 ppm —$\underline{CH}$=$CH_2$ (repeating unit), 4.94 ppm —CH=$\underline{CH_2}$ (repeating unit), 2.12 ppm CH (repeating unit—backbone), 1.27 ppm $CH_2$ (repeating unit—backbone), $CH_2$ and $CH_3$ 3.65 ppm 0.82 ppm—end groups.

| Polymer | Solvent | Mn | Mw | PDI |
|---|---|---|---|---|
| $PB_{12}$ | $CHCl_3$ | 526 | 602 | 1.14 |
| $PB_{12}PMOXA_5$ | $CHCl_3$ | 632 | 738 | 1.19 |

$PB_{12}$-$PMOXA_5$-NH—$(CH_2)$—$NH_2$

NMR

PB: 5.45 ppm —$\underline{CH}$=$CH_2$ (repeating unit), 4.94 ppm —CH=$\underline{CH_2}$ (repeating unit), 2.12 ppm CH (repeating unit—backbone), 1.27 ppm $CH_2$ (repeating unit—backbone), $CH_2$ and $CH_3$ 3.65 ppm 0.82 ppm—end groups. PMOXA: 3.45 ppm (—$\underline{CH_2}$—$\underline{CH_2}$—N—), 2.11 ppm (—N—CO—$\underline{CH_3}$)

EXAMPLE 2: VESICLE PREPARATION $PB_{12}$-$PMOXA_5$-NH—$(CH_2)_2$—$NH_2$ polymer (50 mg) was dissolved in 1 ml chloroform in a round bottom flask (Pyrex 200 ml). Solvent was evaporated on a rotary evaporator under reduced pressure producing a thin film of polymer. Subsequent 3 h high vacuum treatment removed the traces of chloroform. 5 ml of water was further added and stirred at 600 rpm. This way a 10 mg/ml suspension of vesicles was prepared. Upon sampling for characterization (LSM, Stopped-Flow, DLS), the suspension was extruded successively through polycarbonate Track ached filters (Millipore) of 1 μm, 800 nm, 400 nm, 200 nm. At each of the extrusions, the suspension was sampled for characterization.

The vesicles were characterised as follows. Cryogenic transmission electron microscopy (cryo-TEM) was used for particle imaging, and surface functionalization was studied using LSM imaging.

For the cryo-TEM, the microscope was FEI TecnaiG2, TF20. Samples were vitrified using a vitrification robot, Vitrobot™ FEI. Magnification used was 25000× (calibrated 31625×)=scale bar 200 rm.

Figure 1B:
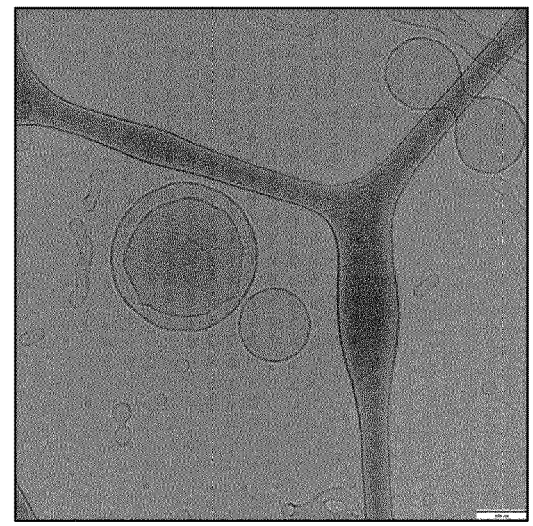

For the LSM imaging, the amine end groups present on the surface of the vesicles prepared as above were allowed to react with tetramethylrhodamine isothiocyanate fluorescent dye (1:1000 molar ratio) and dialyzed against deionized water. Dialysis was performed until dialysate showed no signs of fluorescence, followed by additional change of DI water to eliminate unspecific binding. The vesicles were visualized using a Zeiss LSM 710 Inverted Confocal Microscope with Apochromat 63×/1.4 Oil DIC M27 objective and 561 nm Laser line. Pinhole was varied from 50 um to 70 um. This allowed for the confocal plane to "see through" the vesicles, which thus appear as rims of light (center of vesicle in the center of confocal point) or discs of light (top of the vesicle in confocal point) in suspension where a vesicle floated in and out of focus dynamically. FIGS. 1A and 1B show two sample micrographs clearly showing vesicles.

A secondary approach to investigating vesicle structure is the use of stopped-flow experiments to measure permeability. A stopped flow spectroscope was utilized to mix vesicle suspensions with either hypertonic or hypotonic solutions and the light scattering signal was collected upon deployment of stop syringe. This leads to gradient of concentration across polymer bilayer resulting in water permeation in direction of the gradient. Shrinkage of the polymer vesicles in case of hypertonic and swelling of the polymer vesicles in case of hypotonic solutions is observed. The change in size can be monitored by means of light scattering and the rate at which the change occurs can be attributed to the permeation of water at given size of vesicles. This has been shown also to validate aggregate morphology (A framework for accurate evaluation of the promise of aquaporin based biomimetic membranes M. Grzelakowski, M. F. Cherenet, Y. Shen, M. Kumar Journal of Membrane Science doi: 10.1016/j.memsci.2015.01.023.

Vesicle suspensions were rapidly mixed with osmotic solutions, 1:1 ratio at 16° C. and light scattering signal was collected at 365 nm and at 8 mL/s flow rate. Osmotic water permeability ($P_f$) is calculated from:

$$P_f = \frac{k}{\left(\frac{S}{V_0}\right) \times V_W \times \Delta_{osm}}$$

where k is the initial slope of the light scattering curve corresponding to the change of vesicle diameter with time, S is the initial surface area of the vesicles, $V_0$ is the initial volume of the vesicles, $V_w$ is the molar volume of water, and $\Delta_{osm}$ is the osmolarity difference driving the shrinking of the vesicles.

Figure 2:
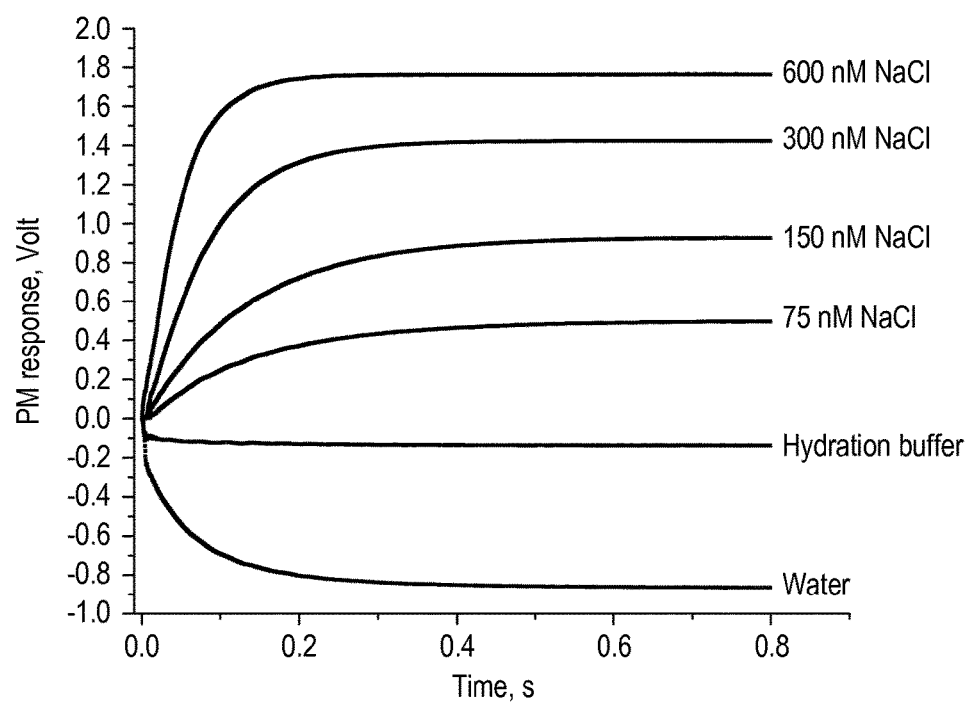
FIGS. 2 and 3 show the results of the stopped-flow experiments of Example 2.

A range of hypertonic solutions was prepared by adding given a given amount of NaCl to hydration buffer (0.1M NaMOPS) resulting in gradients of 600 mM, 300 mM, 150 mM 75 mM, 0 mM (hydration buffer) and −100 mM (pure DI water). As expected and shown in FIG. 2 shrinkage due to hypertonicity was reversed to swelling with hypotonic solution, thus confirming vesicular morphology.

Figure 3:
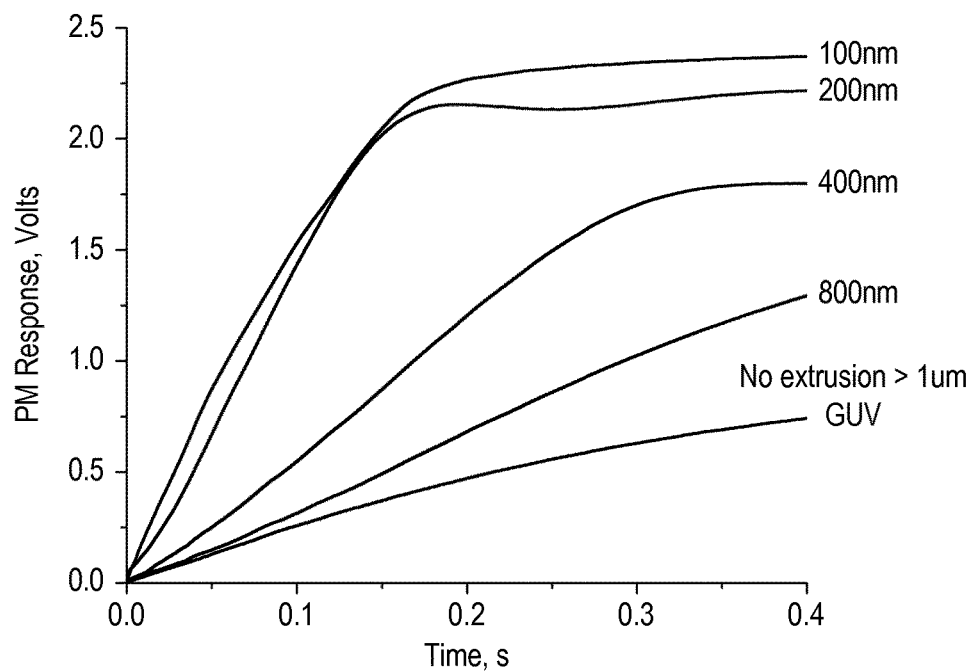

Additionally, stopped flow was also used to confirm the vesicular morphology at every step of extrusion process. The time of the water permeation was proportional to the size of the vesicles exposed to hypertonic condition. The permeability of the bilayer remains constant therefore larger amount of water permeating through larger area of membrane produces longer timeframes. FIG. 3 shows stopped the flow graphs for vesicles extruded through filters with decreasing pore-sizes.

Figure 4:
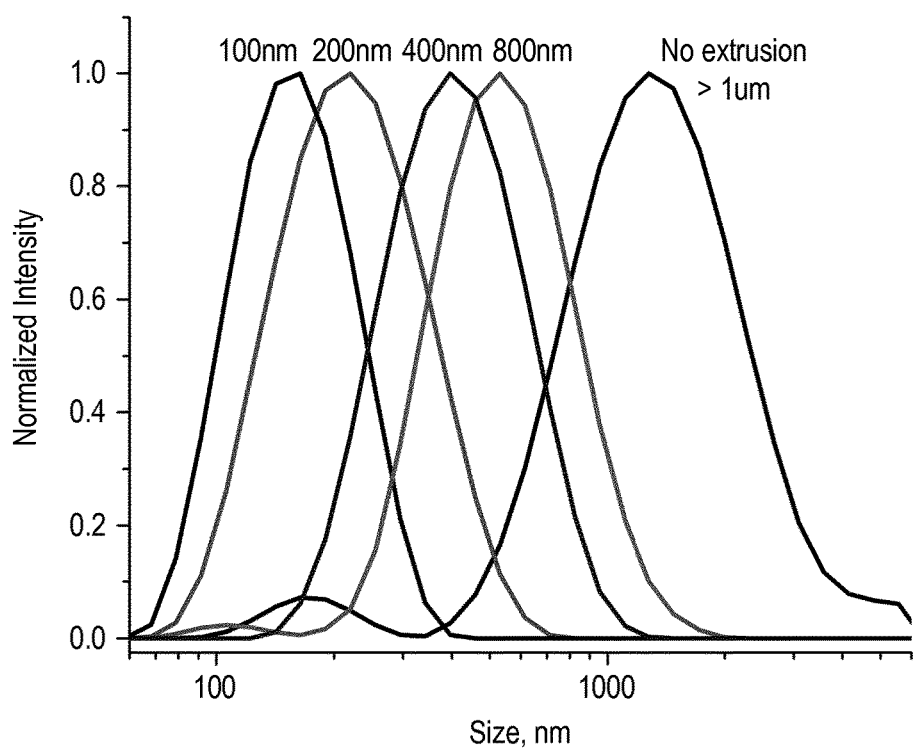
FIG. 4 shows the results of the DLS experiments of Example 2.

Malvern ZetraSizer™ Nano-S dynamic light scattering (DLS) was used to determine particle diameter and size polydispersity index. Vesicle suspensions were left for equilibration overnight before DLS measurements. Afterwards, samples were extruded through membranes with pore sizes 800, 400, 200 and 100 nm. DLS measurements were carried out 6 hours after extrusion. Polystyrene latex was used as the reference material (RI: 1.590; absorption: 0.010 at 633 nm), and water as the dispersant (viscosity: 0.9781 cP; RI: 1.330). The measurements were carried out in Science Brand disposable microcuvettes with a sample volume of 100 µL, at 21° C. Each sample was measured 5 times, each measurement was the average of 11 runs. The results are shown in the table below and in FIG. 4.

| Extrusion | PDI | Mean Size Peak (d · nm) | | |
|---|---|---|---|---|
| | | Intensity | Volume | Number |
| Pre | 0.337 | 1521 | 1327 | 931 |
| 0.8 um | 0.203 | 585.7 | 750.8 | 439.8 |
| 0.4 um | 0.169 | 433.8 | 520.1 | 312.3 |
| 0.2 um | 0.15 | 238.1 | 239.2 | 137.1 |
| 0.1 um | 0.093 | 165.4 | 151.7 | 107.2 |

EXAMPLE 3: INSERTION OF PROTEIN INTO VESICLES

Water permeability of polymer vesicles was enhanced by reconstitution of water channel membrane protein—aquaporin Z. Film hydration procedure was modified to accommodate addition of protein at PoPr 400. Shortly: to the hydrating vesicles protein solution is added at PoPr 400. Next steps follow the protocol of standard vesicles formation.

$PB_{12}$-$PMOXA_5$-$NH$—$(CH_2)_2$—$NH_2$ polymer (50 mg) was dissolved in 1 ml chloroform in a round bottom flask (Pyrex 200 ml). Solvent was evaporated on a rotary evaporator under reduced pressure producing a thin film of polymer. Subsequent 3 h high vacuum treatment removed the traces of chloroform. 5 ml of 100 mM Na-MOPS buffer containing 0.1245 mg of aquaporin Z (Applied Biomimetic) and 0.5% octyl glucoside (O311-n-Octyl-β-D-Glucopyranoside, Anagrade, Anatrace) and was further added and stirred at 600 rpm. 10 mg/ml suspension of proteo-vesicles was extruded trough 200 nm polycarbonate Track ached filter (Millipore). Permeability measurements were performed using stopped-flow spectrometer.

Figure 5:
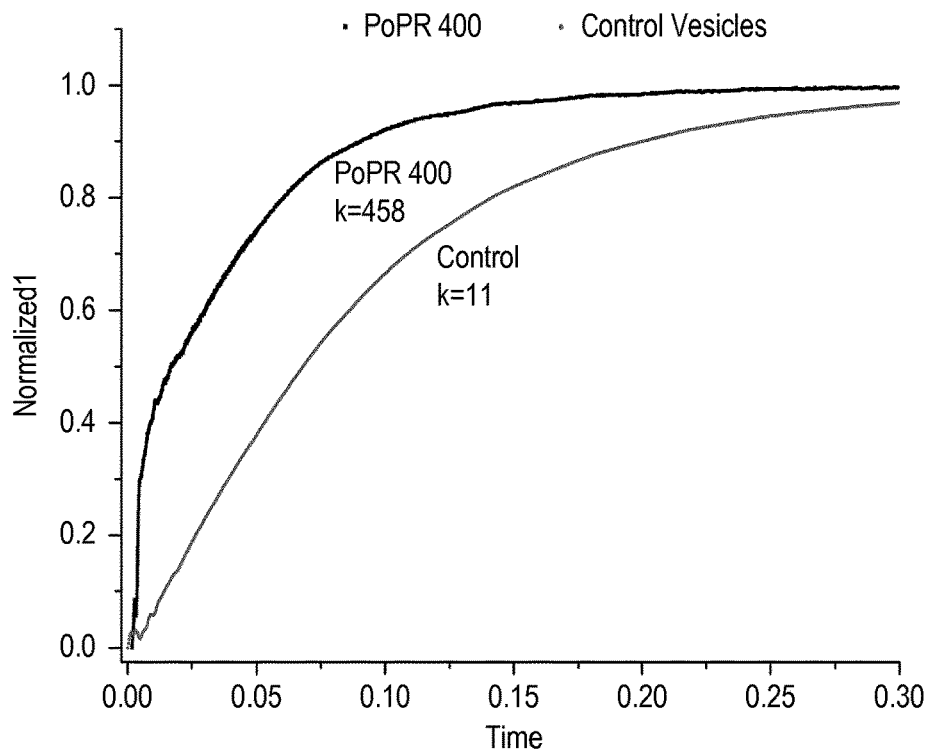
FIG. 5 shows the effect of incorporating Aquaporin Z protein into vesicles according to the invention as described in Example 3.

Stopped flow spectroscopy was used to evaluate protein insertion. This is measured as increase in water permeability of vesicles reconstituted with aquaporin water channel. With the amount of protein added as little as PoPR (polymer to protein ratio) of 400 the increase in water permeability over control vesicles was measured to be 46 times. The results are shown in FIG. 5.

EXAMPLE 4: CORE CROSS-LINKING OF PB-PMOXA VESICLES USING FREE-RADICALS

PB-PMOXA vesicles prepared as in Example 2 were subjected to known amounts of free-radical generating solutions under isotonic conditions in order to cross-link the PB cores and produce less permeable/more rigid structures.

PB-PMOXA was prepared as in Example 1 and made into vesicles using thin-film rehydration in 100 mM NaMOPS pH7.5. Vesicles were then extruded through Millipore Isopore™ membranes of pore size 0.2 µm and tested on a Kintek™ SFLS and ZetasizerNANO™ DLS (Malvern). All chemicals and buffers were purchased from Sigma Aldrich.

Prepared PB-PMOXA vesicles were aliquoted (250 µL) into four 4 mL clear glass vials and set aside to equilibrate at room temperature. Three solutions were prepared in NanoPur water for the cross-linking procedure. 100 mM Potassium Persulfate ($K_2SO_4$) was prepared by dissolving 100 mg in 3.699 mL NanoPur water, 100 mM Sodium Metabisulfite ($Na_2S_2O_5$) by dissolving 100 mg in 5.26 mL NanoPur water, and 100 mM Iron(II) Sulfate Heptahydrate ($FeSO_4 \cdot 7H_2O$) by dissolving 100 mg in 3.597 mL NanoPur water. 2 vials of vesicles were given 50 µL of 100 mM Potassium Persulfate, 25 µL of 100 mM sodium metabisulfite, and 1 μL of 100 mM Iron(II) sulfate heptahydrate while the other two were given 100 μL, 50 μL, and 2 μL respectively. These pairs were then split; one reacting at room temperature, while the other reacted at 70° C. Samples were allowed to react for one hour and then tested on DLS and SFLS for size and permeability after equilibrating to room temperature.

Effectiveness of the cross-linking of the hydrophobic core was manifested by change in the solubility of cross-linked polymer vesicles in organic solvents. Prior to cross-linking, the polymer was soluble in both ethanol and chloroform. After cross-linking, the vesicles had reduced solubility in both. The amount of radical initiating solution added was directly proportional to the decreased solubility of cross-linked material in chloroform.

EXAMPLE 5: MEMBRANE PREPARATION

In this Example, the concentration of deposited vesicles was kept constant and monitored by matching the count rate (250 kcps) in Dynamic Light Scattering (Malvern Zetasizer Nano) with static attenuator.

Sulfo-SANPAH (SS) solution (10 mM in 100 mM NaM-OPS pH 7.5) was allowed to react with previously prepared PB-PMOXA-NH—$(CH_2)_2$—$NH_2$ vesicles in the absence of light (250 μL of vesicle solution combined with 50 μL SS for 15-minutes). A series of 47 mm polysulfone membranes (hand casted) were cut by punch press and placed into Teflon® membrane holders and rinsed with deionized water. Excess water was removed by compressed air and 300 μL (each) of SS-activated vesicle suspensions were placed onto the polysulfone support membranes. The membrane holders were then placed under UV light approximately 5 cm from the source and covered with foil for protection for 30 minutes. Excess reactants were then removed from the membrane surface using a 1 ml pipette without touching the membrane surface. The above steps were repeated three times, following which the membranes were removed from the holders and 25 mm diameter membrane samples were cut from the coated area using a punch press. These were then rinsed in excess 100 mM NaMOPS ph7.5 on a shake table for at least one hour before testing.

Figure 6:
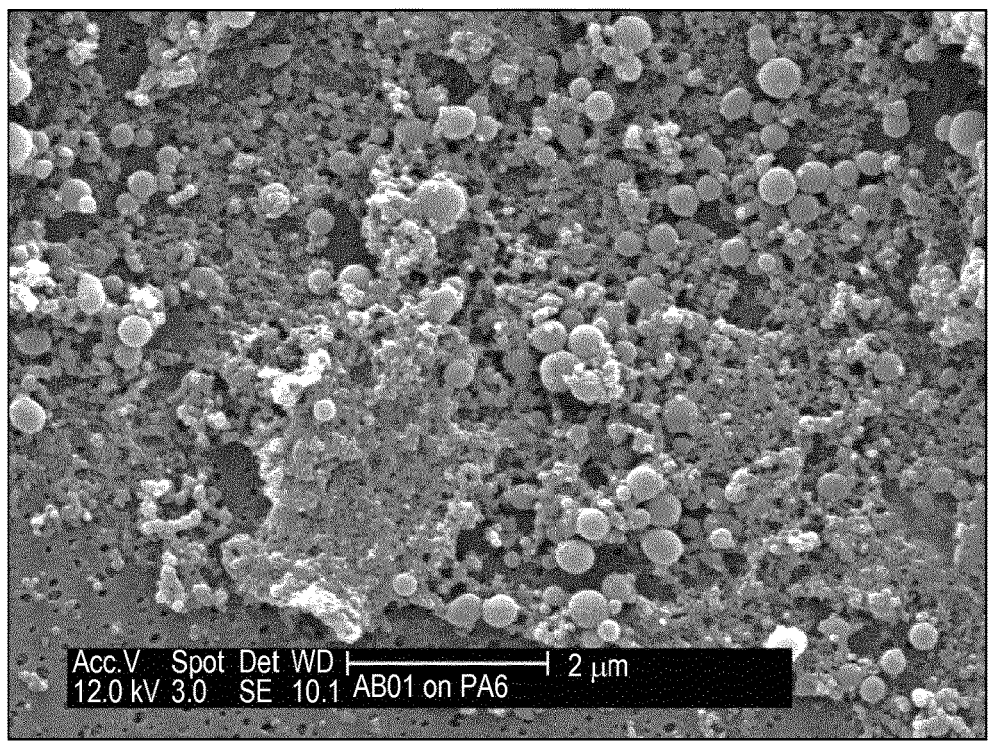
FIG. 6 is a micrograph of the membrane of Example 5.

FIG. 6 is a micrograph of the resulting membrane, showing a coherent mass comprising a plurality of vesicles cross-linked on the surface of the support membrane.

Membranes prepared in the step described above were subject to treatment with either 10 or 150 μL of free radical initiating solution composing of:
25 mM Iron(II) Sulfate Heptahydrate,
25 mM Sodium Metabisulfite,
25 mM Potassium Persulfate The treatment resulted in crosslinking of the PB hydrophobic core.

The resulting membrane samples were tested for pore size distribution using a standard molecular weight cut-off analysis technique. The 25 mm samples prepared in the previous step were tested for their ability to retain high molecular weight materials, by measuring their molecular weight cut-off, i.e. the point at which at least 90% of molecules of a given molecular weight are retained by the membrane. Phosphate buffer (0.03M $Na_2HPO_4$+0.03M $KH_2PO_4$) was pre-filtered using a 0.2 um membrane and the pH was adjusted to 7.2 prior to use for preparation of solutions. Dextran (DXT) standards were dissolved in phosphate buffer (DXT 165 kDa, 325 kDa, 548 kDa, 1300 kDa, and 5000 kDa, DXT 0.505 kDa, 4 kDa, 6 kDa, 11 kDa, 20 kDa, and 28 kDa). All of the dextran solutions were diluted to 0.5 mg/ml with phosphate buffer and pre-filtrated using a 0.2 um polyethersulfone membrane prior to use. All filtration experiments were conducted in a 10 ml Amicon stirred ultrafiltration cell (Model 8010, Millipore Corp.) All samples were evaluated according to the protocol described below:

Filtered 10 ml volume of deionised water at 20 psi to wet the pore structure and the whole system.
  Connected the feed line with dextran solution feed to a digital peristaltic pump (Thermal Fisher Science Inc.), re-pressurized the cell to 20 psi, set the filtrate flux to 5 μm/s.
  Obtained 800 μL samples of the filtrate solution after filtration of 2,000 μL of water for equilibration and washing out the dead volume downstream of the membrane.
  Obtained 1 ml permeate samples directly from the cell after filtration.
  Cleaned and rinsed the whole system with deionised water.
  The stirring speed was kept at 600 rpm and all experiments were performed at room temperature (22±3° C.)

Figure 7:
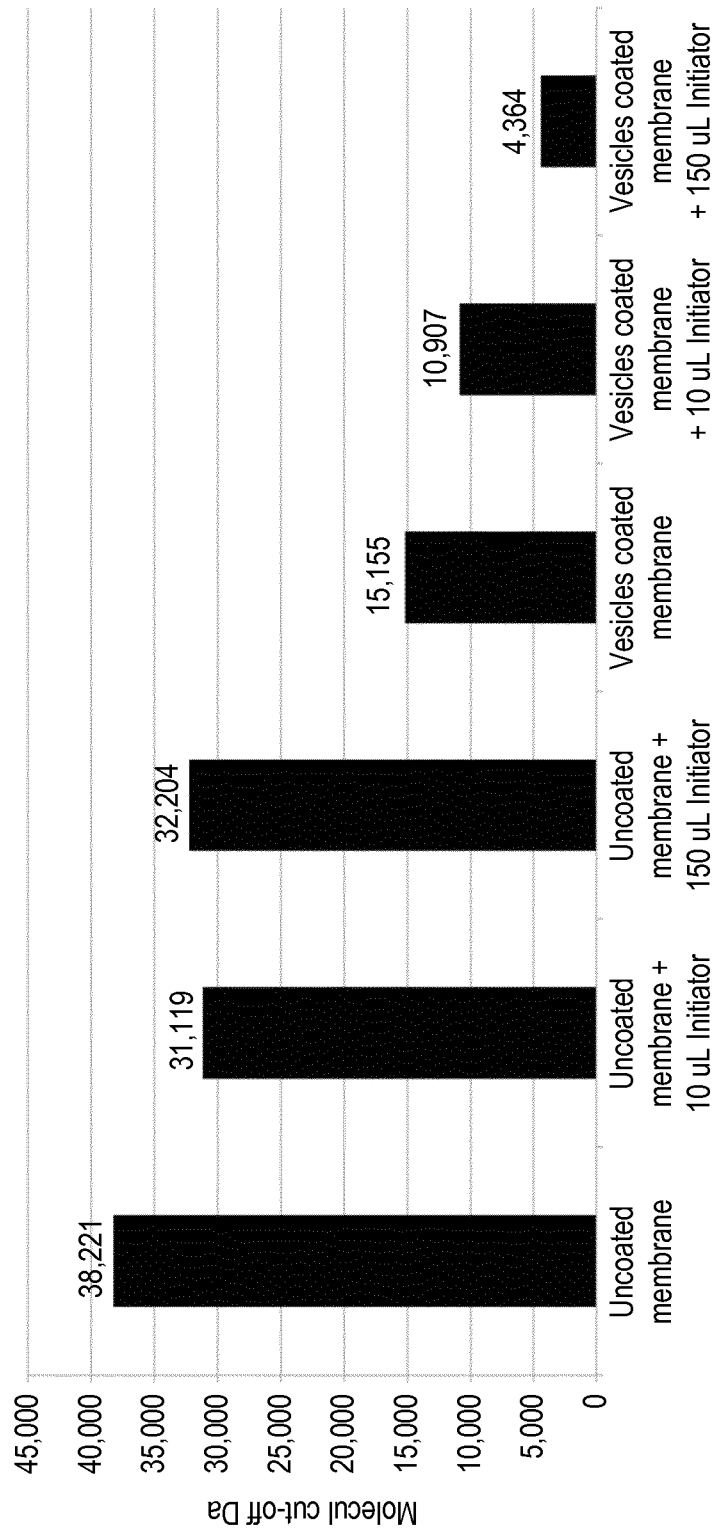
FIG. 7 shows the effect of internally cross-linking the polybutadiene in the membrane of Example 5.

Permeate was further evaluated using high-pressure liquid chromatography (HPLC columns PL1149-6840, MW 10,000 to 200,000, PL1120-6830, MW 100 to 30,000, PL1149-6860, MW 200,000 to >10,000,000). Comparison of the feed to the permeate chromatograms allowed for calculation of retention coefficients and membrane molecular cut-off. The results are shown in FIG. 7, which shows that molecular cut-off of the control membrane was reduced to half when coated with vesicles. Molecular weight cut-off of the vesicle-coated membrane decreased to 4000 Ka upon core-crosslinking of the polybutadiene using initiator. Reduction in molecular cut-off is shown to be dependent on the amount of the cross-linker used.

EXAMPLE 6: ENCAPSULATION EFFICIENCY OF VESICLES

Fluorescein (Sigma-Aldrich F6377) solution 1 mM was prepared in 100 mM sodium-MOPS (GFS 5440). Polymer vesicles were prepared according to Example 2 using fluorescein Na-Mops solution as hydration media. Polymer vesicles were further extruded through polycarbonate Track ached filters (Millipore) at 200 nm. Un-encapsulated dye was removed by dialysis (Thermo Fisher Scientific 66383 10 kDa) against 100 mM sodium-MOPS (1:1000 volume ratio, three changes).

Fluorescence Correlation Spectroscopy (FCS) was used to quantify the number of encapsulated dye molecules per vesicle. The experiments were performed on a time correlated single photon counting (TCSPC) module (Becker-Hickl GmbH, Berlin, Germany). The detailed instrumentation setup is described in Gullapalli et al, "Integrated multimodal microscopy, time-resolved fluorescence, and optical-trap rheometry: toward single molecule mechanobiology", J. Biomedical Optics, 2007 January-February; 12(1):014012. PubMed PMID: 17343487. Pubmed Central PMCID: PMC3251961. Epub 2007/03/09. eng. The light source utilized was a Nd:YAG pulsed laser with an emission maximum of 532 nm. A 60× water immersion objective with a numerical aperture of 1.2 was used to focus the laser beam into a diffraction-limited focal point 40 μm above the cover slip within the sample. Laser power was set to 30 μW/m² by measuring light intensity at the back of the objective aperture.

In an FCS experiment, time-dependent changes in fluorescent intensity within a small observation (confocal) volume (~1 femtoliter) are monitored and the fluctuations are fit to an autocorrelation function described below (Equation 1).

$$G(\tau) = \frac{\langle \delta F(t) \rangle \langle \delta F(t+\tau) \rangle}{\langle F(t) \rangle^2} \quad (1)$$

Here, $G(\tau)$ is the normalized autocorrelation function; $\delta F(t)$ is the fluorescence intensity fluctuation at time t; $\delta F(t+\tau)$ is the fluorescence intensity fluctuation after a time lag $\tau$, and $F(t)$ is the average fluorescence intensity at time t. When $\tau=0$, the term on the right side of the Equation 1 equals the variance of the fluorescence intensity fluctuation, which yields $G(0)=1/N$. N represents the average number of fluorophores in the confocal volume. These principles were used to obtain the concentration of fluorescein in aqueous solutions and polymer vesicles by fitting observed autocorrelation curves from FCS experiments to a 3D diffusion model shown below in Equation 2 and described in Gullapalli et al, above.

$$G(\tau) = \frac{1}{N} \sum_{i=1}^{M} f_i \left[ \frac{1}{1+(\tau/\tau_{D_i})} \right] \left[ \frac{1}{1+(r/z)^2(\tau/\tau_{D_i})} \right]^{1/2} \quad (2)$$

Here, r and z are radius and half height of the confocal volume, which is often assumed to have 3D Gaussian illumination profile, see Maiti et al, Proc. Nat. Acad. Sci., 1997; 94(22): 11753-7. $\tau_{D_i}$ is 2D lateral diffusion time of fluorescent species i across the confocal volume. $f_i$ is the fraction of fluorescent species i. We used a single species fitting for both free fluorescein dye and polymer vesicles with encapsulated dye.

Figure 8:
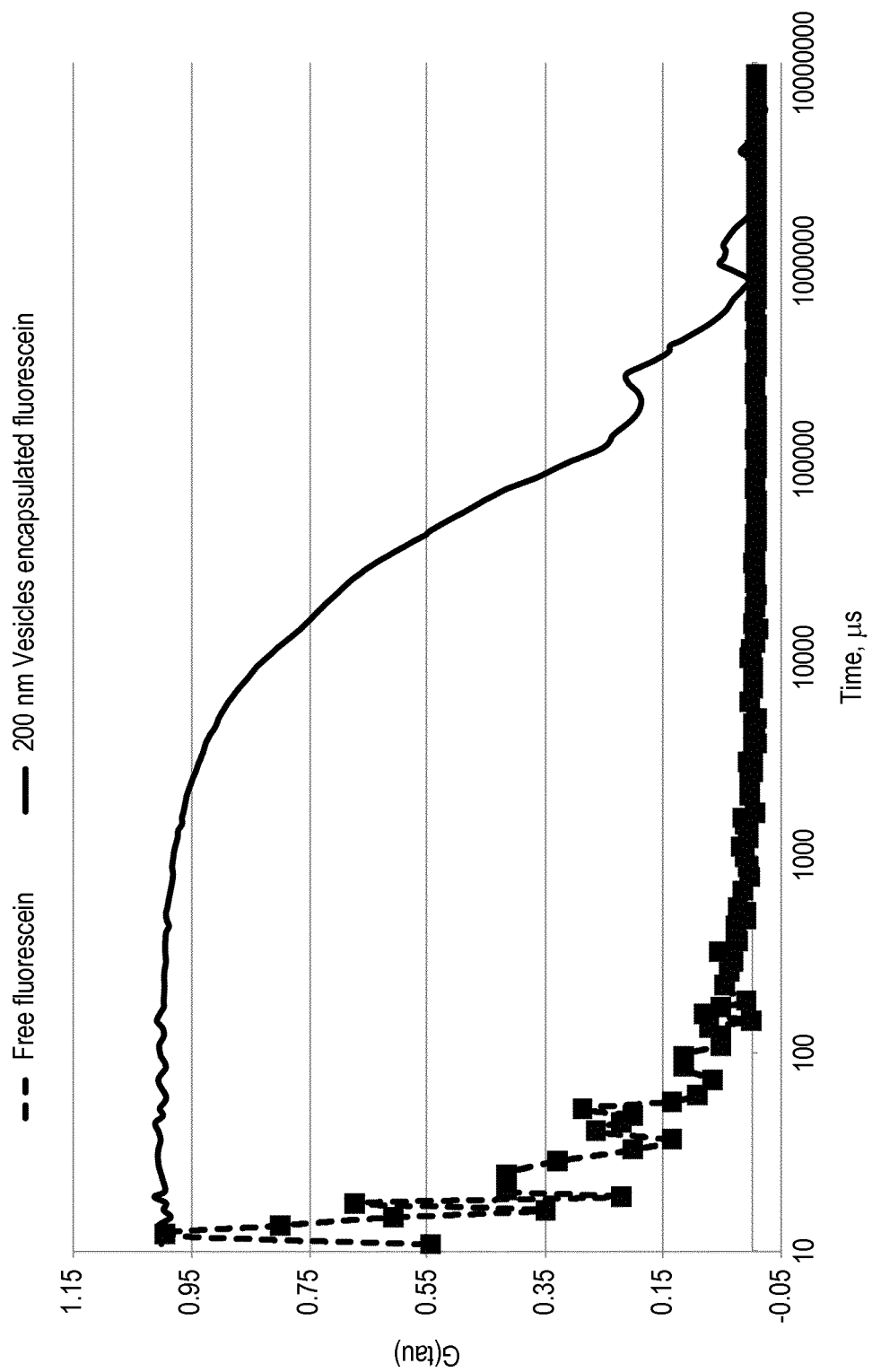
FIG. 8 shows the results of the encapsulation efficiency experiment described in Example 6.

Molecular brightness was measured using method based on FCS as described in Rigler et al, Correlation Spectroscopy, 2006 (9):367-73, to calculate the number of fluorescein molecules per vesicle, $N_{encap\text{-}fluor}$. In this method, free fluorescein molecules in 0.1M Na MOPS buffer (pH=7.5) was used as a standard. Molecular brightness (photons emitted per molecule at standard excitation rate) of fluorescein, $\varepsilon_{fluorescein}$, was measured by dividing total number of collected photons throughout the experiment by the duration of the measurement and dividing that number by the number of fluorescein molecules in the confocal volume, $N_{free\text{-}fluor}$, as obtained by fitting of the time-shifted autocorrelation curve to a 3D diffusion model (Equation 2). The molecular brightness of the fluorescein encapsulated polymer vesicles, $\varepsilon_{polymersome}$, was determined likewise. The ratio of the molecular brightness of the polymer vesicles to the molecular brightness of the free fluorescein, ($\varepsilon_{polymersome}/\varepsilon_{fluorecein}$), yielded an estimate of the number of fluorescein molecules per polymersome, $N_{encap\text{-}flour}\cdot\mu$ The results obtained are shown in FIG. 8. The molecular brightness of fluorescein, $\varepsilon_{fluorescin}$, was 29 photons/molecule/second. The molecular brightness of the polymersomes at 0.2 μm, $\varepsilon_{polmersome}$, was 11244 photons/molecule/second. Hence the number of encapsulated fluorescein molecules per polymersome, $N_{fluorescein}=\varepsilon_{polmersome}/\varepsilon_{fluorescein}$, was 387 molecules. The radius of 200 nm vesicle was corrected for wall thickness (cryo-TEM, R effective=$9.09 \times E^{-08}$ m) and the encapsulation volume of vesicle was calculated to be $3.14 \times E^{-18}$ dm$^3$. 1 mM solution was used in the hydration of polymer vesicles and concentration of fluorescein measured inside of vesicles was 0.204196992 mM. Therefore, these results show a 25% encapsulation efficiency, which is a high figure.

The invention claimed is:

1. A block copolymer comprising at least one (poly)2-C$_{1\text{-}3}$alkyl-2-oxazoline block and at least one polybutadiene block, which is a diblock copolymer AB, in which (poly)2-C$_{1\text{-}3}$alkyl-2-oxazoline forms the A block and polybutadiene forms the B block, and which comprises an end group at the end of a (poly)2-C$_{1\text{-}3}$alkyl-2-oxazoline block wherein the end group is selected from carboxy, activated carboxy, amine, methacrylate, thiol, azide, and alkyne and wherein the B block contains 5 to 15 butadiene units.

2. A block copolymer as claimed in claim 1, in which the number of butadiene units in the B block is at least half the number of 2-C$_{1\text{-}3}$alkyl-2-oxazoline units in the A block.

3. A block copolymer as claimed in claim 2, in which the number of butadiene units in the B block is at least twice the number of 2-C$_{1\text{-}3}$alkyl-2-oxazoline units in the A block.

4. A block copolymer as claimed in claim 1, which contains from 5 to 180 2-C$_{1\text{-}3}$alkyl-2-oxazoline units in the A block.

5. A block copolymer as claimed in claim 1, in which said end group is selected from carboxy, activated carboxy, or an amine end group having the formula —NHR in which R represent an alkyl group having from one to 6 carbon atoms substituted by at least one —NH$_2$ group.

6. A block copolymer as claimed in claim 1, in which the (poly)2-C$_{1\text{-}3}$alkyl-2-oxazoline is (poly)2-methyl-2-oxazoline.

7. Vesicles formed from a block copolymer of claim 1.

8. Vesicles as claimed in claim 7, in which C=C double bonds present in polybutadiene blocks of different block copolymer chains are cross-linked together.

9. Vesicles as claimed in claim 7, having transmembrane proteins incorporated therein.

10. Vesicles as claimed in claim 9, in which the transmembrane protein is an aquaporin.

11. Vesicles as claimed in claim 7, containing a drug or a cosmetic agent.

12. A filtration membrane comprising vesicles as claimed in claim 9.

13. A filtration membrane as claimed in claim 12, which comprises a porous support and, covalently bonded to a surface thereof, a layer comprising a plurality of vesicles formed from the block copolymer, and having transmembrane proteins incorporated therein; and in which within said layer, vesicles are covalently linked together to form a coherent mass.

14. A process for the preparation of a membrane as claimed in claim 13, which comprises providing an aqueous suspension of vesicles formed from the block copolymer, and having transmembrane proteins incorporated therein; depositing said suspension of vesicles on a surface of a porous support; and providing reaction conditions such that covalent bonds are formed between different vesicles and between vesicles and said surface.

15. A process as claimed in claim 14, which comprises either:
 (a) providing an aqueous suspension of vesicles formed from the block copolymer, and having transmembrane proteins incorporated therein, said vesicles being formed from block copolymers having reactive end groups X;

(b) providing a multifunctional linking agent having at least two reactive groups Y which are reactive with polymer end groups X;
(c) depositing said suspension of vesicles and said multifunctional linker on a support having a surface which is reactive with either polymer end groups X or reactive groups Y; and
(d) causing reaction of end groups X with groups Y, and either end groups X or groups Y with the surface of the support; or
(aa) providing a first aqueous suspension of vesicles formed from the block copolymer, and having transmembrane proteins incorporated therein, said vesicles being formed from block copolymers having reactive end groups X;
(bb) providing a second aqueous suspension of vesicles formed from the block copolymer, and having transmembrane proteins incorporated therein, said vesicles being formed from block copolymers having reactive end groups Y which are reactive with polymer end groups X;
(cc) depositing said suspensions of vesicles on a support having a surface which is reactive with either polymer end groups X or Y; and
(dd) causing reaction of end groups X with end groups Y, and either end groups X or end groups Y with the surface of the support.

16. A process as claimed in claim 15, in which said multifunctional linking agent of step (b) is N-sulfosuccinimidyl-6-(4'-azido-2'-nitrophenylamino)hexanoate.

17. A filtration membrane as claimed in claim 12, in which the transmembrane protein is an aquaporin.

18. A membrane as claimed in claim 13, in which the transmembrane proteins are aquaporins.

* * * * *